United States Patent
Simon et al.

(10) Patent No.: US 9,603,954 B2
(45) Date of Patent: Mar. 28, 2017

(54) METHODS FOR GENERATING RADIOIMMUNOCONJUGATES

(75) Inventors: Jaime Simon, Angleton, TX (US); A. Gaylord King, Bartonville, TX (US); Josue Manuel Moreno Bermudez, Ismaning (DE)

(73) Assignee: ACTINIUM PHARMACEUTICALS INC., Florham Park, NJ (US)

( * ) Notice: Subject to any disclaimer, the term of this patent is extended or adjusted under 35 U.S.C. 154(b) by 0 days.

(21) Appl. No.: 13/386,316

(22) PCT Filed: Jul. 22, 2010

(86) PCT No.: PCT/US2010/042885
§ 371 (c)(1),
(2), (4) Date: May 14, 2012

(87) PCT Pub. No.: WO2011/011592
PCT Pub. Date: Jan. 27, 2011

(65) Prior Publication Data
US 2012/0220754 A1   Aug. 30, 2012

Related U.S. Application Data

(60) Provisional application No. 61/227,710, filed on Jul. 22, 2009.

(51) Int. Cl.
*A61K 51/10* (2006.01)

(52) U.S. Cl.
CPC .................. *A61K 51/1027* (2013.01)

(58) Field of Classification Search
CPC .................. A61K 51/1027; A61K 51/1093
See application file for complete search history.

(56) References Cited

U.S. PATENT DOCUMENTS

| | | |
|---|---|---|
| 4,001,387 A | 1/1977 | Barak et al. |
| 4,296,785 A | 10/1981 | Vitello et al. |
| 4,305,922 A | 12/1981 | Rhodes |
| 4,454,106 A | 6/1984 | Gansow et al. |
| 4,472,509 A | 9/1984 | Gansow et al. |
| 4,663,129 A | 5/1987 | Atcher et al. |
| 4,732,864 A | 3/1988 | Tolman |
| 4,816,397 A | 3/1989 | Boss et al. |
| 4,828,991 A | 5/1989 | Hanna, Jr. et al. |
| 4,833,329 A | 5/1989 | Quint et al. |
| 4,894,364 A | 1/1990 | Greer |
| 4,923,985 A | 5/1990 | Gansow et al. |
| 4,946,778 A | 8/1990 | Ladner et al. |
| 5,038,046 A | 8/1991 | Norman et al. |
| 5,246,691 A | 9/1993 | Geerlings et al. |
| 5,254,328 A | 10/1993 | Herscheid et al. |
| 5,292,868 A | 3/1994 | Subramanian |
| 5,296,216 A | 3/1994 | Turner |
| 5,355,394 A | 10/1994 | van Geel et al. |
| 5,428,154 A | 6/1995 | Gansow et al. |
| 5,443,816 A | 8/1995 | Zamora et al. |
| 5,612,016 A * | 3/1997 | Griffiths et al. ............ 424/1.49 |
| 5,641,471 A | 6/1997 | Geerlings |
| 6,010,680 A * | 1/2000 | Govindan et al. .......... 424/1.69 |
| 6,458,933 B1 | 10/2002 | Hansen |
| 6,670,456 B2 | 12/2003 | Frank et al. |
| 7,074,405 B1 | 7/2006 | Hansen et al. |
| 7,374,936 B2 | 5/2008 | Geerlings |
| 2002/0058007 A1 | 5/2002 | Scheinberg et al. |
| 2002/0082389 A1 | 6/2002 | Geerlings |
| 2003/0086868 A1 | 5/2003 | Ma et al. |
| 2006/0058218 A1 | 3/2006 | Syud et al. |
| 2006/0088539 A1 | 4/2006 | Bander |

FOREIGN PATENT DOCUMENTS

| | | |
|---|---|---|
| EP | 0306168 A1 | 3/1989 |
| GB | 2188638 | 10/1987 |
| JP | 2002-516297 A | 6/2002 |
| JP | 2004-527528 A | 9/2004 |
| JP | 2005-523887 A | 8/2005 |
| JP | 2009-509497 A | 3/2009 |
| WO | WO-90/15625 A1 | 12/1990 |
| WO | WO-02/22000 A2 | 3/2002 |
| WO | WO-03/101496 A1 | 12/2003 |
| WO | WO-2007/128557 A1 | 11/2007 |

OTHER PUBLICATIONS

Antczak et al. (Bioconjugate Chem., 17:1551-1560, 2006).*
Mirzadeh et al. (Bioconjugate Chem., 1: 59-65, 1009).*
Roos et al. (Anal. Bioanal. Chem., 392: 1135-1147, published online Jul. 15, 2008).*
Beckford, D. R. et al. (2007) Nuevo radioimmunoconjugado 90Y-DOTA-HR3 Sintesis y radiomarcaje. Nucleus 2007, 41, 3-8 (English Abstract).
Boder, E., 1997, Yeast surface display for screening combinatorial polypeptide libraries, Nat Biotechnol, 15(6):553-7.
Chen, W., Georgiou, G., 2002, Cell-Surface display of heterologous proteins: From high-throughput screening to environmental applications, Biotechnol Bioeng, 79(5):496-503.
Dugas, H., 1989, Bioorganic Chemistry: A chemical approach to enzyme action, Starch-Stärke, Springer-Verlag New-York, 43(4):161.
Hoogenboom, H., 2000, Natural and designer binding sites made by phage display technology, Immunol Today, 21(8):371-8.
Inbar, D., 1972, Localization of antibody-combining sites within the variable portions of heavy and light chains, Proc Natl Acad Sci U.S.A., 69(9):2659-62.
Jones, P., 1986, Replacing the complementarity-determining regions in a human antibody with those from a mouse, Nature, 321:522-525.

(Continued)

*Primary Examiner* — Brad Duffy
*Assistant Examiner* — Nelson B Moseley, II
(74) *Attorney, Agent, or Firm* — Wilmer Cutler Pickering Hale and Dorr

(57) ABSTRACT

Methods for generating an Ac-225 radioconjugate comprising a monoclonal antibody (mAb) (IgG) is disclosed. The Ac-225 radioimmunoconjugate is an [Ac-225]-p-SCN-Bn-DOTA AIHuM195 radioimmunoconjugate.

35 Claims, 15 Drawing Sheets

(56) References Cited

OTHER PUBLICATIONS

Köhler G., Milstein C., 1975, Continuous cultures of fused cells secreting antibody of predefined specificity, Nature, 256(5517):495-7.

Köhler G., Milstein C., 1976, Derivation of specific antibody-producing tissue culture and tumor lines by cell fusion, Eur. J. Immunol., 6(7):511-519.

Krejcarek, G., 1977, Covalent attachment of chelating groups to macromolecules, Biochem. Biophys. Res. Commun., 77(2):581-585.

Kretzschmar, T., von Rüden, T., 2002, Antibody discovery: phage display, Curr Opin Biotechnol, 13(6):598-602.

Lewis, M. R. et al. (1994) A Facile, Water-Soluble Method for Modification of Proteins with DOTA. Use of Elevated Temperature and Optimized pH to Achieve High Specific Activity and High Chelate Stability in Radiolabeled Immunoconjugates. Bioconjugafe Chem. 5, 565-576.

Lewis et al. (2001) an improved method for conjugating monoclonal antibodies with N-hidroxysulfosuccinimimidyl DOTA. Bioconjugate Chem. 12: 320-324.

Lindoy, L., 1989, The chemistry of macrocyclic ligand complexes, J. Chem. Tech. Biotech., Cambridge University Press, 47(4):378.

Lu, S. X. et al. (2005) Mass Spectral Analyses of Labile DOTA-HNS and Heterogeneity Determination of DOTA or DMI Conjugated Anti-PSMA Antibody for Prostate Cancer Therapy. Journal of Pharmaceutical Sciences, vol. 94(4): 788-797.

Mattheakis, L., 1994, An in vitro polysome display system for identifying ligands from very large peptide libraries, Proc Natl Acad Sci U.S.A., 91(19):9022-9026.

Meares, C., 1984, Conjugation of antibodies with bifunctional chelating agents: Isothiocyanate and bromoacetamide reagents, methods of analysis, and subsequent addition of metal ions, Anal. Biochem., 142(1):68-78.

Morrison, S., 1984, Chimeric human antibody molecules: mouse antigen-binding domains with human constant region domains, Proc. Natl. Acad. Sci USA, 81(21):6851-55.

Ogawa, Y. et al. (2007) Quantification of bifunctional diethyenetriaminepentaccetic acid derivative conjugation to monoclonal antibodies by matrix-assisted laser desorption/ionization time of flight mass spectrometry. Analytical Biochemistry 368: 214-221.

Pack, P., 1993, Improved bivalent miniantibodies, with identical avidity as whole antibodies, produced by high cell density fermentation of *Escherichia coli.*, Biotechnology (N.Y.), 11(11):1271-1277.

Pitt, C., 1980, The design of chelating agents for the treatment of iron overload, Inorg. Chem. Bio. Med., American Chemical Society, Washington D.C., 17:279-312.

Sandhu, J., 1992, Protein engineering of antibodies, Crit Rev Biotechnol, 12(5-6):437-62.

Shrikant V. D., et al. (1990) Yttrium-90-Labeled monoclonal antibody for therapy: Labeling by new macrocyclic bifunctional chelating agent. J Nucl Med. 31, 473-479.

Smith, G., 1985, Filamentous fusion phage: novel expression vectors that display cloned antigens on the virion surface, Science, 228(4705):1315-1317.

Whitlow, M., 1991, Single-chain Fv proteins and their fusion proteins in Methods: A Companion to Methods in Enzymology, 2:97-105.

Borrebaek, et al., "An improved labeling method for Thorium-227 labeled antibodies for targeted alpha therapy," J. Nucl. Med. 2009; 50 (Suppl. 2): 1821; abstract only.

Brechbiel, M. and Gansow, O.A., "Synthesis of C-Functionalized trans-Cyclohexyldiethylenetriaminepenta-acetic Acids for Labelling of Monoclonal Antibodies with the Bismuth-212 α-Particle Emitter," J. Chem. Soc. Perkin Trans., vol. 1, pp. 1173-1178 (1992).

Brown, I., "Astatine-211: Its Possible Applications in Cancer Therapy," Appl. Radiat. Isot., vol. 37, No. 8, pp. 789-798 (1986).

Chatterjee, M. et al., "Idiotypic antibody immunotherapy of cancer," Cancer Immunol. Immunopathol, vol. 38, pp. 75-82 (1994).

Curti, Brendan D., "Physical barriers to drug delivery in tumors," Critical Reviews in Oncology/Hematology, vol. 14, pp. 29-39 (1993).

Delikan, Orhan, "Preparation of $^{224}$Ra for Therapy, of Ankylosing Spondylitis," Health Physics, vol. 35, No. 1, pp. 21-24 (1978).

Denardo, G.L. et al., "Fractionated Radioimmunotherapy of B-Cell Malignancies with $^{131}$I-Lym-1," Cancer Research (Suppl.), vol. 50, pp. 1014s-1016s (Feb. 1, 1990).

Fischer, D.R., "Alpha Particle Emitters in Medicine", Presented at the Dosimetry of Administered Radionuclides, Washington, DC, pp. 194-214 (Sep. 21 and 22, 1989).

Goldenberg, David M., "Targeting of Cancer with Radiolabeled Antibodies: Prospects for Imaging and Therapy," Arch Pathol Lab Med, vol. 112, pp. 580-587 (Jun. 1988).

International Search Report and Written Opinion mailed on Sep. 14, 2010 for corresponding International Patent Application No. PCT/US2010/042885 (10 pages).

Jain, Rakesh K., "Barriers to Drug Delivery in Solid Tumors," Scientific American, vol. 271, No. 1, 9 pages (Jul. 1994).

Kozak, R. W. et al., "Radionuclide-conjugated monoclonal antibodies: a synthesis of immunology, inorganic chemistry and nuclear science," TIBTECH, vol. 4, No. 10, 6 pages (Oct. 1986).

Lambrecht, Richard M., "Radionuclide Generators", Radiochemica Acta, vol. 34, pp. 9-24, (1983).

Macklis, R. M. et al. "Radioimmunotherapy with Alpha-Particle-Emitting Immunoconjugates," Science, vol. 240, No. 4855, pp. 1024-1026 (1988).

McDevitt M.R. et al., "Design and synthesis of $^{225}$Ac radioimmunopharmaceuticals," Applied Radiation and Isotopes, vol. 57, No. 6, pp. 841-847 (2002).

Miederer M.D. et al., "Pharmacokinetics, Dosimetry, and Toxicity of the Targetable Atomic Generator, $^{225}$Ac-HuM195, in Nonhuman Primates," The Journal of Nuclear Medicine, vol. 45, No. 1, pp. 129-137 (Jan. 2004).

Mirzadeh, S. et al., "Radiometal Labeling of Immunoproteins: Covalent Linkage of 2-(4-Isothiocyanatobenzyl) diethylenetriaminepentaacetic Acid Ligands to Immunoglobulin," Bioconjugate Chem., vol. 1, pp. 59-65 (1990).

Mitsugashira, T. et al., "Preparation of Traces for Actinium, Thorium, Proactinium and Uranium, SPEY", Min. Educ. Sci. & Cult, Tokyo, vol. 91, pp. 111-116 (1984).

Nikula, T. K. et al., "Alpha-Emitting Bismuth Cyclohexylbenzyl DTPA Constructs of Recombinant Humanized Anti-CD33 Antibodies: Pharmacokinetics, Bioactivity, Toxicity and Chemistry," The Journal of Nuclear Medicine, vol. 40, No. 1, 11 pages (Jan. 1999).

Osband, M.E. et al., "Problems in the investigational study and clinical use of cancer immunotherapy," Immunology Today, vol. 1, No. 6, 3 pages (1990).

Riechmann, L. et al., "Reshaping human antibodies for therapy," Nature, vol. 332, No. 24, pp. 323-327 (1988).

Rotmensch, J. et al., "Estimates of Dose to Intraperitoneal Micrometastases from Alpha and Beta Emitters in Radioimmunotherapy," Gynecologic Oncology, vol. 38, No. 3, pp. 478-485(1990).

Scheinberg, D. A. et al., "Targeting in Erythroleukemic Mice: Radioiodinated and Chelated Radiometal-Conjugated Monoclonal Antibody," Department of Pharmacology and Experimental Therapeutics, The Johns Hopkins University School of Medicine, pp. 159-171 (1982).

Spitsyn, V. I. et al., "Generators for the Production of Short-Lived Radioisotopes," Atomic Energy Review, vol. 9, No. 4, 5 pages, International Atomic Energy Commission Vienna (1971).

Suzuki, S. et al., "Solution Chemistry of Light Actinude Elements," Japan/US Seminar on Torium fuel reactors Proceedings, Nara, Japan pp. 137-143 (Oct. 18-22, 1982).

Wilbur, D. Scott, "Potential Use of Alpha Emitting Radionucleotldes in the Treatment of Cancer," Antibody, Immunoconjugates and Radiopharmaceuticals, vol. 4, No. 1, pp. 85-97 (1991).

Zwierzina, Heinz, "Practical Aspects of Cytokine Therapy," Stem Cells, vol. 11, pp. 144-153 (1993).

(56) References Cited

OTHER PUBLICATIONS

Supplementary European Search Report issued by the European Patent Office for Application No. 10802893.7, PCT/US2010042885, mailed on Aug. 18, 2014 (7 pages).
Japanese Office Action issued by the Japanese Patent Office for Application No. 2012-521780 dated Nov. 17, 2014 (7 pages).
McDevitt, M.R. et al., "Tumor therapy with targeted atomic nanogenerators," Science, vol. 294, No. 5546, pp. 1537-1540 (Nov. 16, 2001).
Nikula, T.K. et al., "A Rapid, Single Vessel Method for Preparation of Clinical Grade Ligand Conjugated Monoclonal Antibodies," Nucl. Med. Biol., vol. 22, No. 3, pp. 387-390, 5 pages (1995).
McDevitt, M. R. et al., "An $^{225}$Ac/$^{213}$Bi generator system for therapeutic clinical applications: construction and operation," Applied Radiation and Isotopes, vol. 50, pp. 895-904 (1999).
McDevitt, M. R. et al., "Preparation of α-Emitting $^{213}$Bi-Labeled Antibody Constructs for Clinical Use," The Journal of Nuclear Medicine, vol. 40, No. 10, pp. 1722-1727 (Oct. 1999).
Sgouros, G. et al., "Pharmacokinetics and Dosimetry of an α-Particle Emitter Labeled Antibody: $^{213}$Bi-HuM195 (Anti-CD33) in Patients with Leukemia," The Journal of Nuclear Medicine, vol. 40, No. 11, pp. 1935-1946 (Nov. 1999).
Maguire et al., "Efficient one-step radiolabeling of monoclonal antibodies to high specific activity with Actinium-225 for alpha-particle radioimmunotherapy of cancer," *J Nucl Med.* 55(9): 1492-1498 (2014).
Extended European Search Report issued by the European Patent Office for European Patent Application No. 10802893.7 dated Jul. 29, 2014 (9 pgs.).

\* cited by examiner

METHODS FOR GENERATING RADIOIMMUNOCONJUGATES

This application is a U.S. National Phase Application Under 35 U.S.C. §371 of International Patent Application No. PCT/US2010/042885 filed Jul. 22, 2010, which claims the benefit of U.S. Provisional Patent Application No. 61/227,710 filed Jul. 22, 2009, each of which is incorporated herewith in its entirety.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All publications, patent applications, patents, and other references mentioned herein are incorporated by reference in their entirety. The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference. In the case of inconsistencies, the present disclosure will prevail.

BACKGROUND OF THE INVENTION

Radioimmunoconjugates can be used in diagnostic and therapeutic medical procedures. Radiopharmaceuticals can carry at least one radionuclide bound to a carrier, for example a targeting moiety. The radionuclide can produce a signal detectable by radiological diagnostic equipment. Because the radiation emitted by the radionuclide can have a toxic effect on tissues, the radioimmunoconjugates can be utilized to achieve one or more therapeutic effects. When used as a therapeutic agent, localization of the radioimmunoconjugates at a specific structure or site in the body can be used to concentrate the effects of the radioimmunoconjugate in a structures or sites to be treated and can reduce harmful effects at other structures and sites in the body. For example, a radioimmunoconjugate may be used as a chemotherapy drug to kill cancerous tissues. There is a need for improved methods for the production of radioimmunoconjugates. This invention addresses this need.

SUMMARY OF THE INVENTION

In one aspect, the methods described herein relate to a method for producing an actinium-225 (Ac-225) radioconjugate, the method comprising the steps of: (a) conjugating a chelating agent to a biological molecule in a conjugation reaction mixture to generate a conjugated biological molecule, (b) purifying the reaction mixture so as to remove unconjugated chelating agents, and (c) chelating one or more Ac-225 radionuclides with the conjugated biological molecule in a chelation reaction mixture to generate a Ac-225 radioconjugate.

In one embodiment, the conjugating in step (a) comprises incubating the conjugation reaction mixture for about 1.5 hours at about 37° C. In another embodiment, the conjugating in step (a) comprises incubating the conjugation reaction mixture for about 24 hours at about 16° C. to about 20° C.

In still a further embodiment, the purifying comprises filtering the conjugation reaction mixture through a filter so as to purify the conjugated biological molecule.

In one embodiment, the conjugation reaction mixture comprises a bicarbonate buffer. In another embodiment, the conjugation reaction mixture comprises a phosphate buffer. In still a further embodiment, the conjugation reaction mixture has a pH of about 8.0 to about 9.2.

In one embodiment, the filtering is performed in a HEPES buffer. In another embodiment, the filtering is performed in a NaAc buffer. In still a further embodiment, the filtering comprises a molecular weight cut off at least about 10,000 Da, at least about 20,000 Da, or at least about 40,000 Da.

In one embodiment, the chelation reaction mixture comprises gentisic acid or ascorbic acid.

In another embodiment, the chelation reaction mixture has a pH of about 5.5 to about 7.0.

In yet another embodiment, the chelating in step (c) comprises incubating the one or more Ac-225 radionuclides with the conjugated biological molecule for about 1.5 hours at about 37° C.

In another embodiment, the method further comprises a step of adding a termination chelator to the chelation reaction mixture. In one embodiment, the termination chelator is diethylenetriamine-pentaacetic acid (DTPA). In yet another embodiment, the method further comprises a step of incubating the chelation reaction mixture for about 30 minutes at about 37° C. following the step of adding the termination chelator.

In one embodiment, the biological molecule comprises a protein, a peptide, a polynucleotide, a combination thereof, or a derivative thereof.

In one embodiment, the biological molecule is an antibody, an antigen-binding fragment thereof, a single-chain protein comprising the antigen-binding polypeptide sequences of an antibody, a single-domain antibody, an analog of any of the foregoing, or a derivative of any of the foregoing. In another embodiment, the antigen binding fragment is a monoclonal antibody variable region. In still another embodiment, the biological molecule is a protein comprising an antigen binding sequence of an antibody. In yet another embodiment, the biological molecule is a naturally, synthetically, or recombinantly produced protein comprising an antigen binding sequence of an antibody that binds an antigen on the surface of a cell. In yet another embodiment, the antigen on the surface of the target cell is CD-33. In still another embodiment, the biological molecule is HuM195.

In one embodiment, the radioconjugate is a radioimmunoconjugate.

In another embodiment, the chelating agent is a bifunctional chelating agent. In one embodiment, the bifunctional chelating agent is S-2-(4-Isothiocyanatobenzyl)-1,4,7,10 tetraazacyclododecanetetraacetic acid (p-SCN-Bn-DOTA). In another embodiment, the chelating agent is selected from the group of compounds consisting of diethylenetriamine-pentaacetic acid ("DTPA"); 1,4,7,10-tetraazacyclododecane-N,N',N'',N'''-tetraacetic acid ("DOTA"); p-isothiocyanatobenzyl-1,4,7,10-tetraazacyclododecan-1,4,7,10-tetraacetic acid ("pSCN-Bz-DOTA"); 1,4,7,10-tetraazacyclododecane-N,N',N''-triacetic acid ("DO3A"); 1,4,7,10-tetraazacyclododecane-1,4,7,10-tetrakis(2-propionic acid) ("DOTMA"); 3,6,9-triaza-12-oxa-3,6,9-tricarboxymethylene-10-carboxy-13-phenyl-tridec-anoic acid ("B-19036"); 1,4,7-triazacyclononane-N,N',N''-triacetic acid ("NOTA"); 1,4,8,11-tetraazacyclotetradecane-N,N',N'',N'''-tetraacetic acid ("TETA"); triethylene tetraamine hexaacetic acid ("TTHA"); trans-1,2-diaminohexane tetraacetic acid ("CYDTA"); 1,4,7,10-tetraazacyclododecane-1-(2-hydroxypropyl)-4,7,10-triacetic acid ("HP-DO3A"); trans-cyclohexanediamine tetraacetic acid ("CDTA"); trans(1,2)-cyclohexane diethylene triamine pentaacetic acid ("CDTPA"); 1-oxa-4, 7,10-triazacyclododecane-N,N',N''-triacetic acid ("OTTA"); 1,4,7,10-tetraazacyclododecane-1,4,7,10-tetrakis {3-(4-carboxyl)-butanoic acid}; 1,4,7,10-tetraazacyclododecane-1,4,7,10-tetrakis(acetic acid-methyl amide); 1,4,7,10-tetraazacyclododecane-1,4,7,10-tetrakis(methylene phosphonic acid); 2,2',2''-(10-(2-(2,5-dioxopyrrolidin-1-yloxy)-2-oxoethyl)-1,4,7,10-tetraazacyclododecane-1,4,7-triyl)triacetic acid (DOTA-NHS ester) and derivatives, analogs, and mixtures thereof.

In another aspect, the methods described herein relate to a method for producing an [Ac-225]-p-SCN-Bn-DOTA/HuM195 radioimmunoconjugate, the method comprising the steps of: (a) conjugating p-SCN-Bn-DOTA to a HuM195 antibody in a conjugation reaction mixture comprising a bicarbonate buffer and having a pH of about 8.0 to about 9.2, for about 1.5 hours at about 37° C. to generate a p-SCN-Bn-DOTA/HuM195 immunoconjugate, (b) filtering the conjugation reaction mixture through a filter having a molecular weight cut off at least about 10,000 Da, at least about 20,000 Da, or at least about 40,000 Da so as to purify the p p-SCN-Bn-DOTA/HuM195 immunoconjugate, wherein the filtering is performed with a HEPES buffer or NaAc buffer, (c) chelating one or more actinium-225 radionuclides with the p-SCN-Bn-DOTA/HuM195 immunoconjugate in a chelation reaction mixture comprising gentisic acid and having a pH of about 5.5 to about 7.0, for about 1.5 hours at about 37° C. to generate an [Ac-225]-p-SCN-Bn-DOTA/HuM195 radioimmunoconjugate, (d) adding DTPA to the chelation reaction mixture, and (e) incubating the chelation reaction mixture for about 30 minutes at about 37° C.

In certain embodiments, the methods described herein further comprise a step of size-exclusion chromatography through a size exclusion resin before the filtering of step (b). In one embodiment, the size exclusion resin has a size exclusion limit of about 5000 Da.

In certain embodiments, the methods described herein further comprise purifying radionconjugate or the [Ac-225]-p-SCN-Bn-DOTA/HuM195 radioimmunoconjugate by size exclusion chromatography through a size exclusion resin. In one embodiment, the size exclusion resin has a size exclusion limit of about 6000 Da. In another embodiment, the size exclusion resin has a size exclusion limit of about 5000 Da.

In another aspect, the invention relates to a radioimmunoconjugate produced by the methods described herein.

DETAILED DESCRIPTION OF THE INVENTION

Figure 1A:
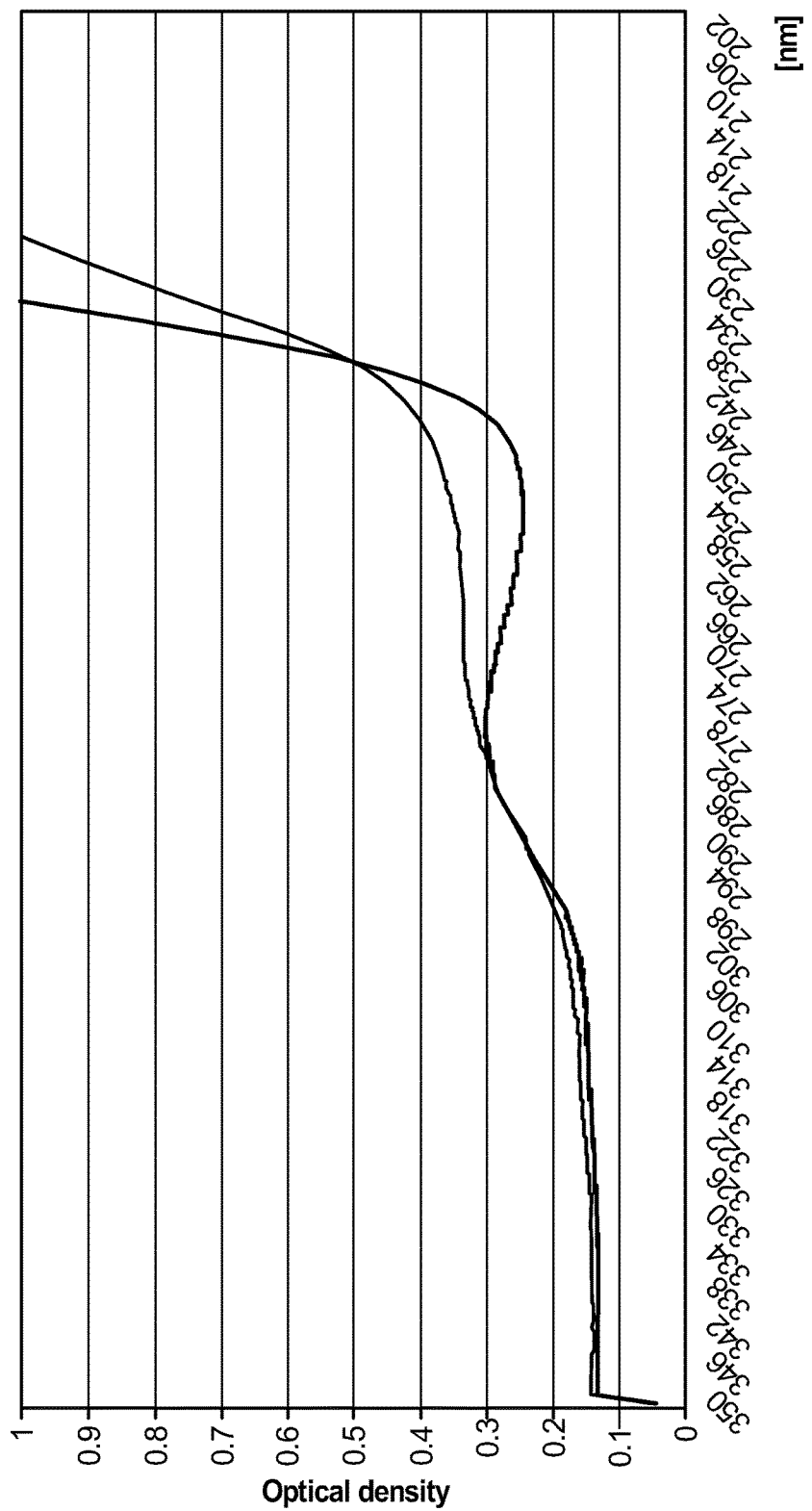
FIG. 1A UV—spectrum of native Hum-195 in pink and of Hum-195/DOTA conjugate in blue. Both solutions had a concentration of app. 100 µg/mL; absorbance was measured using cuvette of 1 cm optical path.

The invention provides methods for generating a radioimmunoconjugate. In one aspect, the invention relates to an improved method for labeling a monoclonal antibody (mAb) (IgG). In one embodiment, the methods is a "post labeling or one step approach".

In one aspect, the methods described herein relate to a one step chelation post conjugation process for the manufacture of a radioimmunoconjugate. In one embodiment, the radioimmunoconjugate is a [Ac-225]-p-SCN-Bn-DOTA/IgG (HuM195) construct.

The radioimmunoconjugates described herein can be prepared by first forming a conjugated targeting moiety and then chelating a radionuclide with the conjugated targeting moiety to form a radioimmunoconjugate. The conjugated targeting moiety may be radiolabeled at any time following conjugation to the targeting moiety.

In one embodiment, the mAb is first conjugated with a DOTA bifunctional chelating agent and then, the purified conjugate is labeled with Ac-225. According to some embodiments described herein, only one single step involving $^{225}$Ac is needed to label the biological molecule. Advantages of the methods described herein over two step or relabeling processes include, but are not limited to consistent higher labeling yields, simplicity, and shorter labeling times. In addition, scale up of the methods described herein can be more readily performed as compared to two step or relabeling processes. Also, the methods described herein are useful for the preparation of a kit formulation where the final radiolabeling can occur at the clinical site.

In one embodiment, HuM-195/p-SCN-Bn-DOTA conjugates are prepared by reacting a concentrated solution of HuM-195 with p-SCN-Bn-DOTA in bicarbonate or in phosphate buffers at pH between about 8 and about 9 and by incubation at either about 37° C. or at room temperature. In another embodiment, bioconjugates can be purified from excess of the bifunctional chelator by repeated filtration or centrifugation and by gravity Size Exclusion Chromatography (SEC). During the purification process, the bicarbonate or phosphate buffer is changed to N-2-Hydroxyethylpiperazine-N-2-ethanesulfonic acid (HEPES; Free Acid) or acetate medium. Conjugates can be characterized by size exclusion high performance liquid chromatography (SE-HPLC).

For labeling, a mixture of HuM-195 and $^{225}$Ac solution in acetate buffer having pH of about 5.5 to about 7.0 is incubated for about 80 to about 90 minutes in the presence of small quantities of a free radical scavenger. After the reaction and challenge with DTPA, the labelling yield can be determined by instant thin layer chromatography (ITLC). The sample mixture can then purified by gravity size exclusion chromatography (SEC). In the purified protein fraction, the amount of $^{225}$Ac and protein can be measured by non-destructive high resolution gamma spectrometry and UV spectrophotometry, respectively. Radiochemical purity in the purified fraction is measured by ITLC and/or SE-HPLC.

In one aspect, the invention comprises radioimmunoconjugates having a CD33 targeting moiety. According to the invention, the targeting moiety can be a synthetic or a natural protein or a portion or variant (including species, allelic and mutant variants) thereof. In some embodiments targeting moieties include antibody moieties.

The radioimmunoconjugates produced using the methods described herein may be used in diagnostic or therapeutic medical procedures. For example, the radiopharmaceutical may be used as an imaging contrast agent to produce PET or other radiographic images. Alternatively, the radiopharmaceutical may be used as a therapeutic agent that delivers doses of radiation to specific structures or sites of physiological activity in the body. One skilled in the art will appreciate other pharmacological uses of the radiopharmaceutical.

In another aspect, the invention provides a method for treating a cancer in a subject, the method comprising administering to the subject a pharmaceutically effective amount of a radioimmunoconjugate.

In yet another aspect, the invention provides a method for treating a cancer in a subject, the method comprising administering to the subject a pharmaceutically effective amount of a pharmaceutical composition, wherein the composition comprises a radioimmunoconjugate that specifically binds to a CD33 molecule on the surface of a cell.

Definitions

As used herein and in the appended claims, the singular forms "a," "an," and "the" include plural references unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. The term "about" is used herein to modify a numerical value above and below the stated value by a variance of 20%.

As used herein the term "purity" refers to the presence of substantially a single chemical entity or the absence of substantial contaminants in a mixture.

The purity of the conjugated molecule produced by the disclosed methods may be measured using standard analytical methods, for example, high performance liquid chromatography (HPLC) or filter purification. When purity is measured by determining the amount of conjugated targeting moiety or radioimmunoconjugate, the purity can be greater than about 70%, greater than about 80%, greater than about 90%, greater than about 95%, greater than about 96%, greater than about 97%, greater than about 98%, or greater than about 99%. When the purity is measured by determining the amount of contamination, contaminants such as unconjugated chelating agents may be less than about 20%, less than about 10%, or less than about 1%.

The term "biological molecule" as used herein refers to carbon-containing molecules, including macromolecules, and includes any molecule known to be found in biological systems, including, amino acids, antibodies, proteins, peptides, nucleic acids (including DNA and RNA), saccharides, polysaccharides and the like. Biological molecules include those which are naturally occurring as well as well as derivatives, analogues and modifications of such molecules. In addition, the term refers to carbon-containing molecules such as pharmaceuticals, antibiotics and the like which are used in medicine. Nucleic acid analogues containing modified bases not found in nature are included as biological molecules. Similarly, any analogue of a molecule found in nature or any chemical modification of such a molecule is also included in the definition of biological molecules. Biological molecules may be isolated from natural sources or synthesized in the laboratory, as, for example, synthetic proteins, peptides or oligonucleotides.

As used herein, the term "targeting moiety" refers to any protein, antibody, antibody fragment, hormone, peptide, growth factor, antigen, hapten or any other carrier which functions to recognize a specific biological target site. Antibody and antibody fragment refers to any polyclonal, monoclonal, chimeric, human, mammalian, single chains, dimeric and tetrameric antibody or antibody fragment. Such biological carrier, when attached to a functionalized complex, serves to carry the attached radionuclide to specific targeted tissues.

The term "antibody" refers to any polyclonal, monoclonal, chimeric antibody or heteroantibody. The antibodies used in the radionuclide conjugates of the present invention are monoclonal antibodies having high specificity for the desired cancer cells. Antibodies used in the present invention may be directed against, for example, cancer, tumors, leukemias, autoimmune disorders involving cells of the immune system, normal cells that need to be ablated such as bone marrow and prostate tissue, virus infected cells including HIV, mycoplasma, differentiation and other cell membrane antigens, pathogen surface antigens and any biologically active molecules.

Some examples of antibodies suitable for use with the methods described herein include, but are not limited to, are HuM195 (anti-CD33), CC-11, CC-46,CC-49, CC-49 F(ab')$_2$, CC-83, CC-83 F(ab')$_2$, and B72.3. Antibody fragment includes Fab fragments and F(ab')$_2$ fragments, and any portion of an antibody having specificity toward a desired epitope or epitopes. The antibodies which may be used in the radionuclide conjugates of the present invention can be prepared by techniques well known in the art. Highly specific monoclonal antibodies can be produced by hybridization techniques well known in the art, see, for example, Kohler and Milstein, Nature, 256, 495-497 (1975); and Eur. J. Immunol., 511-519 (1976).

As used herein, the term "radioconjugate" refers to a biological molecule conjugate labeled with a radionuclide (e.g. one in which the chelating agent moiety of the protein conjugate has formed a complex with a radionuclide).

As used herein, the term "radioimmunoconjugate" refers to a targeting moiety conjugate labeled with a radionuclide (e.g. one in which the chelating agent moiety of the protein conjugate has formed a complex with a radionuclide).

When forming the radioimmunoconjugate described herein, the degree of chelation and conjugation is advantageously high.

As used herein, the terms "degree of conjugation" and "conjugation yield" are used interchangeably and are defined to mean the percentage of the chelant that is successfully conjugated with a targeting moiety divided by the total chelant used in the conjugation reaction. The percent conjugation when making the conjugated targeting moiety of the present reaction is greater than 50%, more greater than 70%, greater than 90%, greater than 95%, greater than about 96%, greater than about 97%, greater than about 98%, or greater than about 99%.

As used herein, the terms "degree of chelation" and "chelation yield" are used interchangeably and are defined to mean the percentage of the a radionuclide that is successfully chelated with a conjugated targeting moiety divided by the total radionuclide used in the chelation reaction. The percent chelation when making the radioimmunoconjugate of the present reaction is greater than 50%, more greater than 70%, greater than 90%, greater than 95%, greater than about 96%, greater than about 97%, greater than about 98%, or greater than about 99%.

As descried herein, production a degree of conjugation and the degree of chelation can depend on one or more parameters of the radioimmunoconjugate preparation process.

According to the methods described herein, a targeting moiety may be dissolved in a buffered solution comprising a chelant. The pH may be selected to optimize conditions for conjugation of the chelant with the targeting moiety in a conjugation reaction mixture. In one embodiment, the conjugation reaction mixture can comprise a bicarbonate buffer. In another embodiment, the conjugation reaction mixture can comprise a phosphate buffer. In still another embodiment, the conjugation reaction mixture can have a pH of about 8.0 to about 9.2. For example, the conjugation reaction mixture can have a pH of about 8.0, about 8.1, about 8.3, about 8.4, about 8.5, about 8.6, about 8.7, about 8.8, about 8.9, about 9.0, about 9.1, or about 9.2. The temperature of the conjugation reaction mixture also may be adjusted to promote conjugation of the chelant with the targeting moiety. In one embodiment, the conjugation reaction mixture can be incubated at a temperature of about 37° C. In still a further embodiment, the conjugation reaction mixture can be incubated for about 1.5 hours.

In another embodiment, a conjugated targeting moiety may be dissolved in a buffered solution comprising a radionuclide. The pH may be selected to optimize conditions for chelation of the radionuclide with the conjugated targeting moiety in a chelation reaction mixture. In one embodiment, the chelation reaction mixture can comprise gentisic acid. In another embodiment, the chelation reaction mixture can have a pH of about 5.5 to about 7.0. For example, the chelation reaction mixture can have a pH of about 5.5, about 5.6, about 5.7, about 5.8, about 5.9, about 6.0, about 6.1, about 6.2, about 6.3, about 6.4, about 6.5, about 6.6, about 6.7, about 6.8, about 6.9 or about 7.0.

The temperature of the chelation reaction mixture also may be adjusted to promote chelation of the radionuclide with the conjugated targeting moiety. In one embodiment, the chelation reaction mixture can be incubated at a temperature of about 37° C. In still a further embodiment, the chelation reaction mixture can be incubated for about 1.5 hours. After a period of time, the solution can be quenched by the addition of a quenching chelate (e.g. diethylenetriaminepentaacetic acid (DTPA)) and the reaction mixture can be purified. In one embodiment, the chelation reaction mixture can be further incubated after addition of the quenching chelate. In one embodiment, the chelation reaction mixture can be further incubated for about 30 minutes after addition of the quenching chelate. In another embodiment, the chelation reaction mixture can be further incubated at about 37° C. after addition of the quenching chelate.

Chelators

Bifunctional chelators are compounds which have the dual functionality of sequestering metal ions plus the ability to covalently bind a biological carrier having specificity for tumor cell epitopes or antigens. Such compounds are of utility for therapeutic and diagnostic applications when they are, for example, complexed with radioactive metal ions and covalently attached to a specific antibody. These types of complexes have been used to carry radioactive metals to tumor cells which are targeted by the specificity of the attached antibody [see, for example, Mears et al., Anal. Biochem. 142, 68-74 (1984); Krejcarek et al., Biochem. And Biophys. Res. Comm. 77, 581-585 (1977)].

Numerous chelators are known in the art. See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Exemplary chelators suitable for the preparation of the radioimmunoconjugates described herein include, but are not limited to chelators such as S-2-(4-Isothiocyanatobenzyl)-1,4,7,10 tetraazacyclododecanetetraacetic acid (p-SCN-Bn-DOTA), diethylene triamine pentaacetic acid (DTPA); ethylene diamine tetraacetic acid (EDTA); 1,4,7,10-tetraazacyclododecane-N,N',N'',N'''-tetraacetic acid (DOTA); p-isothiocyanatobenzyl-1,4,7,10-tetraazacyclododecane-1,4,7, 10-te-traacetic acid (p-SCN-Bz-DOTA); 1,4,7,10-tetraazacyclododecane-N,N',N''-triacetic acid (DO3A); 1,4, 7,10-tetraazacyclododecane-1,4,7,10-tetrakis(2-propionic acid) (DOTMA); 3,6,9-triaza-12-oxa-3,6,9-tricarboxymethylene-10-carboxy-13-phenyl-tridecanoic acid ("B-19036"); 1,4,7-triazacyclononane-N,N',N''-triacetic acid (NOTA); 1,4,8,11-tetraazacyclotetradecane-N,N',N'',N'''-tetraacetic acid (TETA); triethylene tetraamine hexaacetic acid (TTHA); trans-1,2-diaminohexane tetraacetic acid (CYDTA); 1,4,7,10-tetraazacyclododecane-1-(2-hydroxypropyl)-4,7,10-triacetic acid (HP-DO3A); trans-cyclohexanediamine tetraacetic acid (CDTA); trans(1,2)-cyclohexane dietylene triamine pentaacetic acid (CDTPA); 1-oxa-4,7,10-triazacyclododecane-N,N',N''-triacetic acid (OTTA); 1,4,7, 10-tetraazacyclododecane-1,4,7,10-tetrakis{3-(4-carboxyl)-butanoic acid}; 1,4,7,10-tetraazacyclododecane-1,4,7,10-tetrakis(acetic acid-methyl amide); 1,4,7,10-tetraazacyclododecane-1,4,7,10-tetrakis(methylene phosphonic acid); and derivatives thereof.

Radionuclides

The radionuclide complexed with the conjugated targeting moiety may be from any appropriate metallic radioisotope including, but not limited to, actinium-225, astatine-211, iodine-120, iodine-123, iodine-124, iodine-125, iodine-126, iodine-131, iodine-133, bismuth-212, arsenic-72, bromine-75, bromine-76, bromine-77, indium-110, indium-111, indium-113m, gallium-67, gallium-68, strontium-83, zirconium-89, ruthenium-95, ruthenium-97, ruthenium-103, ruthenium-105, mercury-107, mercury-203, rhenium-186, rhenium-188, tellurium-121 m, tellurium-122m, tellurium-125m, thulium-165, thulium-167, thulium-168, technetium-94m, technetium-99m, fluorine-18, silver-111, platinum- 197, palladium-109, copper-62, copper-64, copper-67, phosphorus-32, phosphorus-33, yttrium-86, yttrium-90, scandium-47, samarium-153, lutetium-177, rhodium-105, praseodymium-142, praseodymium-143, terbium-161, holmium-166, gold-199, cobalt-57, cobalt-58, chromium-51, iron-59, selenium-75, thallium-201, and ytterbium-169.

The method of obtaining $^{225}$Ac radionuclide is not critical to the present invention. For example, $^{225}$Ac can be prepared in a cyclotron. $^{225}$Ac can be obtained in pure form from Department of Energy (DOE), U.S.A., and Institute for Transuranium Elements (ITU), Karlsruhe, Germany.

Purification

In certain embodiments, the methods described herein comprise one or more steps of separating a conjugated targeting moiety or a radioimmunoconjugate from other constituents of a reaction mixture. In one embodiment, a mixture can be transferred to a to a filtering device (e.g. a Millipore centrifugal device) having a particular molecular weight cut off such that filtration of the reaction mixture through the filtration device can separate separating a conjugated targeting moiety or a radioimmunoconjugate from other constituents of a reaction mixture. In one embodiment, filtration of reaction mixture can be used to obtain a conjugated targeting moiety or a radioimmunoconjugate having at least about 60%, at least about 65%, at least about 70%, at least about 75%, at least about 80%, at least about 85%, at least about 90%, %, at least about 95%, at least about 97%, at least about 98%, at least about 99%, or at least about 99.5% purity.

In various embodiments, the yield of the conjugated targeting moiety or the radioimmunoconjugate is at least about 70%, at least about 75%, at least about 80%, at least about 85%, or at least about 90%, at least 95%, at least 96%, at least 97%, at least 98%, or at least 99% of the final product.

Targeting Moieties

The targeting moieties described herein can comprise one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (V1) and variable heavy chain (VH) refer to these light and heavy chains respectively.

Antibodies can exist as intact immunoglobulins or as a number of well characterized fragments produced by digestion with various peptidases. In particular, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the F(ab)'2 dimer into an Fab' monomer. The Fab' monomer is essentially an Fab with part of the hinge region (see, Fundamental Immunology, W. E. Paul, ed., Raven Press, N.Y. (1993) for more antibody fragment terminology). While the Fab' domain is defined in terms of the digestion of an intact antibody, one of skill will appreciate that such Fab' fragments may be synthesized de novo either chemically or by utilizing recombinant DNA methodology.

The Fab' regions can be derived from antibodies of animal (especially mouse or rat) or human origin or may be chimeric (Morrison et al., Proc Natl. Acad. Sci. USA 81, 6851-6855 (1984)) or humanized (Jones et al., Nature 321, 522-525 (1986), and published UK patent application No. 8707252).

As described herein, an antibody can include or be derived from any mammal, such as but not limited to, a human, a mouse, a rabbit, a rat, a rodent, a primate, or any combination thereof and includes isolated human, primate, rodent, mammalian, chimeric, humanized and/or complementarity determining region (CDR)-grafted or CDR-adapted antibodies, immunoglobulins, cleavage products and other portions and variants thereof.

Antibodies useful in the embodiments of the invention can be derived in several ways well known in the art. In one aspect, the antibodies can be obtained using any of the hybridoma techniques well known in the art, see, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, Antibodies, A Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

The antibodies may also be obtained from selecting from libraries of such domains or components, e.g. a phage library. A phage library can be created by inserting a library of random oligonucleotides or a library of polynucleotides containing sequences of interest, such as from the B-cells of an immunized animal or human (Smith, G. P. 1985. Science 228: 1315-1317). Antibody phage libraries contain heavy (H) and light (L) chain variable region pairs in one phage allowing the expression of single-chain Fv fragments or Fab fragments (Hoogenboom, et al. 2000, Immunol Today 21(8) 371-8). The diversity of a phagemid library can be manipulated to increase and/or alter the immunospecificities of the monoclonal antibodies of the library to produce and subsequently identify additional, desirable, human monoclonal antibodies. For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in a CDR of the variable region of the immunoglobulin polypeptide, and subsequently screened for desirable affinity and neutralization capabilities. Antibody libraries also can be created synthetically by selecting one or more human framework sequences and introducing collections of CDR cassettes derived from human antibody repertoires or through designed variation (Kretzschmar and von Ruden 2000, Current Opinion in Biotechnology, 13:598-602). The positions of diversity are not limited to CDRs but can also include the framework segments of the variable regions or may include other than antibody variable regions, such as peptides.

Other target binding components which may include other than antibody variable regions are ribosome display, yeast display, and bacterial displays. Ribosome display is a method of translating mRNAs into their cognate proteins while keeping the protein attached to the RNA. The nucleic acid coding sequence is recovered by RT-PCR (Mattheakis, L. C. et al. 1994. Proc Natl Acad Sci USA 91, 9022). Yeast display is based on the construction of fusion proteins of the membrane-associated alpha-agglutinin yeast adhesion receptor, aga1 and aga2, a part of the mating type system (Broder, et al. 1997. Nature Biotechnology, 15:553-7). Bacterial display is based fusion of the target to exported bacterial proteins that associate with the cell membrane or cell wall (Chen and Georgiou 2002. Biotechnol Bioeng, 79:496-503).

In comparison to hybridoma technology, phage and other antibody display methods afford the opportunity to manipulate selection against the antigen target in vitro and without the limitation of the possibility of host effects on the antigen or vice versa.

Specific examples of antibody subsequences include, for example, Fab, Fab', (Fab')$_2$, Fv, or single chain antibody (SCA) fragment (e.g., scFv). Subsequences include portions which retain at least part of the function or activity of full length sequence. For example, an antibody subsequence will retain the ability to selectively bind to an antigen even though the binding affinity of the subsequence may be greater or less than the binding affinity of the full length antibody.

An Fv fragment is a fragment containing the variable region of a light chain VL and the variable region of a heavy chain VH expressed as two chains. The association may be non-covalent or may be covalent, such as a chemical cross-linking agent or an intermolecular disulfide bond (Inbar et al., (1972) Proc. Natl. Acad. Sci. USA 69:2659; Sandhu (1992) Crit. Rev. Biotech. 12:437).

A single chain antibody ("SCA") is a genetically engineered or enzymatically digested antibody containing the variable region of a light chain VL and the variable region of a heavy chain, optionally linked by a flexible linker, such as a polypeptide sequence, in either VL-linker-VH orientation or in VH-linker-VL orientation. Alternatively, a single chain Fv fragment can be produced by linking two variable domains via a disulfide linkage between two cysteine residues. Methods for producing scFv antibodies are described, for example, by Whitlow et al., (1991) In: Methods: A Companion to Methods in Enzymology 2:97; U.S. Pat. No. 4,946,778; and Pack et al., (1993) Bio/Technology 11:1271.

Other methods of producing antibody subsequences, such as separation of heavy chains to form monovalent light-heavy chain fragments, further cleavage of fragments, or other enzymatic, chemical, or genetic techniques may also be used, provided that the subsequences bind to the antigen to which the intact antibody binds.

Antibodies used in the invention, include full length antibodies, subsequences (e.g., single chain forms), dimers, trimers, tetramers, pentamers, hexamers or any other higher order oligomer that retains at least a part of antigen binding activity of monomer. Multimers can comprise heteromeric or homomeric combinations of full length antibody, subsequences, unmodified or modified as set forth herein and known in the art. Antibody multimers are useful for increasing antigen avidity in comparison to monomer due to the multimer having multiple antigen binding sites. Antibody multimers are also useful for producing oligomeric (e.g., dimer, trimer, tertamer, etc.) combinations of different antibodies thereby producing compositions of antibodies that are multifunctional (e.g., bifunctional, trifunctional, tetra-functional, etc.).

Antibodies can be produced through chemical crosslinking of the selected molecules (which have been produced by synthetic means or by expression of nucleic acid that encode the polypeptides) or through recombinant DNA technology combined with in vitro, or cellular expression of the polypeptide, and subsequent oligomerization. Antibodies can be similarly produced through recombinant technology and expression, fusion of hybridomas that produce antibodies with different epitopic specificities, or expression of multiple nucleic acid encoding antibody variable chains with different epitopic specificities in a single cell.

Antibodies may be either joined directly or indirectly through covalent or non-covalent binding, e.g. via a multimerization domain, to produce multimers. A "multimerization domain" mediates non-covalent protein-protein interactions. Specific examples include coiled-coil (e.g., leucine zipper structures) and alpha-helical protein sequences. Sequences that mediate protein-protein binding via Van der Waals' forces, hydrogen bonding or charge-charge bonds are also contemplated as multimerization domains. Additional examples include basic-helix-loop-helix domains and other protein sequences that mediate heteromeric or homomeric protein-protein interactions among nucleic acid binding proteins (e.g., DNA binding transcription factors, such as TAFs). One specific example of a multimerization domain is p53 residues 319 to 360 which mediate tetramer formation. Another example is human platelet factor 4, which self-assembles into tetramers. Yet another example is extracellular protein TSP4, a member of the thrombospondin family, which can form pentamers. Additional specific examples are the leucine zippers of jun, fos, and yeast protein GCN4.

Antibodies may be directly linked to each other via a chemical cross linking agent or can be connected via a linker sequence (e.g., a peptide sequence) to form multimers.

In one embodiment, the methods described herein relate to a targeting moiety that specifically binds CD33 and includes at least a portion of the humanized V regions. For example, the antibody can include a VL region as defined and a VH region having at least one humanized fragment.

Pharmaceutical Compositions

In the practice of the present invention the radioimmunoconjugate conjugate may be administered per se or as a component of a pharmaceutically acceptable formulation.

As used herein, "pharmaceutically acceptable salt" means any salt of a compound of formula I which is sufficiently non-toxic to be useful in therapy of mammals. Representative of those salts, which are formed by standard reactions, from both organic and inorganic sources include, for example, sulfuric, hydrochloric, phosphoric, acetic, succinic, citric, lactic, maleic, fumaric, palmitic, cholic, palmoic, mucic, glutamic, d-camphoric, glutaric, glycolic, phthalic, tartaric, formic, lauric, steric, salicylic, methane-sulfonic, benzenesulfonic, sorbic, picric, benzoic, cinnamic and other suitable acids. Also included are salts formed by standard reactions from both organic and inorganic sources such as ammonium, alkali metal ions, alkaline earth metal ions, and other similar ions. Preferred are the salts of the compounds of formula I where the salt is potassium, sodium, ammonium, or mixtures thereof.

As used herein, the term "therapeutically effective amount" means an amount of a radioimmunoconjugate that produces a therapeutic effect on the disease treated. The therapeutically effective amount will vary depending on the mammal, the radioimmunoconjugate and the method of its administration (for example, oral or parenteral). A person of ordinary skill in the art can determine the therapeutically effective amount of the radioimmunoconjugate.

Pharmaceutical compositions include "pharmaceutically acceptable" and "physiologically acceptable" carriers, diluents or excipients. As used herein the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary active compounds (e.g., preservatives, antibacterial, antiviral and antifungal agents) can also be incorporated into the compositions.

Pharmaceutical compositions can be formulated to be compatible with a particular local or systemic route of administration. Thus, pharmaceutical compositions include carriers, diluents, or excipients suitable for administration by particular routes.

Specific non-limiting examples of routes of administration for compositions of the invention are inhalation or intranasal delivery. Additional routes include oral, nasal, parenteral, e.g., intravenous, intradermal, subcutaneous, oral, transdermal (topical), and transmucosal administration.

Pharmaceutical compositions comprising the radioimmunoconjugates described herein can be prepared according to standard techniques and further comprise a pharmaceutically acceptable carrier. Generally, normal saline can be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of the radioimmunoconjugates described herein, in the pharmaceutical formulations can vary widely, i.e., from about 0.05% to about 1% by weight, about 1% to about 2% by weight, about 2% to about 5% by weight, about 5% to about 10% by weight, about 10% to about 30% by weight, about 30% to about 50% by weight, about 50% to about 75% by weight, about 75% to about 99% by weight. Pharmaceutical compositions can be selected according to their physical characteristic, including, but not limited to fluid volumes, viscosities and other parameters in accordance with the particular mode of administration selected. For example, the concentration may be increased to lower the fluid load associated with treatment. The amount of radioimmunoconjugates administered will depend upon the particular targeting moiety used, the disease state being treated, the therapeutic agent being delivered, and the judgment of the clinician. Generally the amount of radioimmunoconjugate administered will be sufficient to deliver a therapeutically effective dose of the particular pharmacological agent. Therapeutically effective dosages for various pharmacological agents are well known to those of skill in the art and representative ranges are given for a number of pharmaceuticals above. Typical radioimmunoconjugate dosages can be between about 0.001 and about 50 mg per kilogram of body weight, or between about 0.1 and about 10 mg/kg of body weight. Therapeutically effective dosages can also be determined at the discretion of a physician.

The radioimmunoconjugate pharmaceutical compositions can be administered parenterally, i.e., intraarticularly, intravenously, intraperitoneally, subcutaneously, intramuscularly, orally or nasally. Particular formulations which are suitable for this use are found in Remington's Pharmaceutical Sciences, Mack Publishing Company, Philadelphia, Pa., 17th ed. (1985). The formulations can comprise a solution of the radioimmunoconjugate suspended in an acceptable carrier, or an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

For transmucosal or transdermal administration, penetrants appropriate to the barrier to be permeated can be used in the formulation. Such penetrants are generally known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds can be formulated into ointments, salves, gels, or creams as generally known in the art.

Additional pharmaceutical formulations appropriate for the compositions for administration in the methods of the invention are known in the art (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; and Pharmaceutical Principles of Solid Dosage Forms, Technonic Publishing Co., Inc., Lancaster, Pa., (1993)).

The pharmaceutical formulations can be packaged in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the pharmaceutical carrier or excipient.

Kits

The current invention also provides kits comprising a radioimmunoconjugate generated according to the methods described herein. The targeting moieties of radioimmunoconjugates in the kit may be monoclonal or polyclonal in nature. One or both arms of the targeting moiety of the kit may be chimeric, human, humanized, or deimmunized.

The kit as provided by the current application may also include a clearing composition that will clear the unbound radioimmunoconjugates from the tissue. One suitable clearing agent is a glycosylated anti-idiotypic Fab' fragment targeted against the disease targeting arm(s) of the targeting moiety of the radioimmunoconjugate. In this embodiment, a radioimmunoconjugate is given and allowed to accrete in targets to its maximum extent. To clear the residual radioimmunoconjugate, an anti-idiotypic Ab to the target Ab is given as a glycosylated Fab' fragment. The clearing agent binds to the radioimmunoconjugate in a monovalent manner, while its appended glycosyl residues direct the entire complex to the liver, where rapid metabolism takes place. Clearing agents are discussed in greater detail in U.S. Ser. Nos. 09/314,135 and 09/337,756.

The following examples illustrate the present invention, and are set forth to aid in the understanding of the invention, and should not be construed to limit in any way the scope of the invention as defined in the claims which follow thereafter.

EXAMPLES

Example 1

Nomenclature and Definitions

P-SCN-Bn-DOTA: S-2-(4-Isothiocyanatobenzyl) 1,4,7, 10 tetraazacyclododecanetetraacetic acid (Macrocyclics, Dallas, Tex.)
BFC: Bifunctional chelating agents
DOTA-BFC: DOTA bifunctional chelating agents: e.g. NHS-DOTA; p-SCN-Bn-DOTA
Na ($NH_4$) Ac: Sodium (ammonium) acetate
mAb: Monoclonal antibody: HuM-195
HuM-195: Anti-CD33 antibody construct for therapy of myeloid leukemia. HuM-195 is a recombinant IgG1 mAb combining CDR regions of murine M-195 with human framework/constant regions.
SEC: Size exclusion chromatography
HPLC: High performance liquid chromatography
SE-HPLC/UV: SE-HPLC coupled with an UV detector
SE-HPLC/rad.: SE-HPLC coupled with a radioactive detector
ITLC: Instant thin layer chromatography
$NH_4CH_3CO_2$: Ammonium acetate, $NH_4Ac$
$NaCH_3CO_2$: Sodium acetate, NaAc
$D_f$: Dilution factor
CHCA: Alpha-cyano-4-hydroxycinnamic acid
MALDI: Matrix-assisted laser desorption/ionization mass spectrometry
HDPE: High density polyethylene
HEPES: N-2-Hydroxyethylpiperazine-N-2-ethanesulfonic acid

Example 2

Conjugation of HuM195 with p-SCN-Bn-DOTA 2.3.1 Materials and chemicals. See Table 2 for specifications
2.3.2 Preparation of chemicals and conditions for the conjugation reaction
2.3.2.1 Prepare in Advance the Following Solutions:
Native HuM195, 5 mg/mL, stored at 4-8° C.
p-SCN-Bn-DOTA, stored at −20° C.

NaCl, 0.9%: Weigh 0.45 g NaCl and dissolve it in free metal water, then bring the volume to 50 mL. Mix the solution and after homogenization filter it through a 0.45 μm cellulose acetate membrane filter. Keep the solution in a 50 mL-HDPE container 0.2 M sodium phosphate monobasic (solution A): Weigh 0.48 g NaH2PO4 and add to 20 mL of distilled H2O. Mix the solution until total dissolution 0.2 M sodium phosphate dibasic (solution B): Weigh 2.83 g NaHPO4 and add 100 mL of distilled H2O 0.1 M Phosphate buffer, pH=8: Combine and mix 5.3 mL of solution A with 94.7 mL of solution B. To test the pH, use pH paper. Dilute buffer by adding an equal volume of distilled H2O~100 mL. Filter the solution through a 0.45 μm cellulose acetate membrane filter. Keep the solution in a 50 mL-HDPE container 2 M NaOH: Take about 5 mL of the 30% NaOH and mix it with free metal water, let cool the solution and then bring the volume to 25 mL. Keep the solution in a 50 mL-FEP container 4M NaOH: In a 50 ml HDPE container add 50 ml of metal free water and 8.0 g of NaOH and agitate to dissolve completely.

3 M NH4Ac (or NaAc): Weigh 6.15 g NaAc and dissolve in free metal water. After dissolution of the salt, bring the volume to 25 mL. Mix the solution and after homogenization filter it through a 0.45 μm cellulose acetate membrane filter. Keep the solution in a 25 mL-HDPE container 0.25 M NH4Ac (or NaAc): Take 2.1 mL of the 3 M NaAc and mix with free metal water, bring the volume to 25 mL. Mix the solution and after homogenization filter it through a 0.45 μm cellulose acetate membrane filter. Keep the solution in a 25 mL-HDPE container 0.1 M NH4Ac (NaCH3CO2), pH 7. Take 3.3 mL of the 3 M NaAc and mix with free metal water, bring the volume to 100 mL. Keep the solution in a 100 mL-HDPE container 0.1 M HCl: Take 2.5 mL of 10 M HCl and mix with metal free water in a 25 mL PE volumetric flask. Wait until the solution is cooled and bring the volume to 25 mL. Mix the solution and after homogenization filter it through a 0.45 μm cellulose acetate membrane filter. Keep the solution in a 25 mL-HDPE container 0.05 M HCl: Take 1.25 mL of 10 M HCl and mix with metal free water in a 25 mL PE volumetric flask. Wait until the solution is cooled and bring the volume to 25 mL. Mix the solution and after homogenization filter it through a 0.45 μm cellulose acetate membrane filter. Keep the solution in a 25 mL-HDPE container NaN3 0.05%. Weigh 0.5 g NaN3 and dissolve it in Millipore water. Bring the volume to 1 L.

1.0 M NaHCO3. In a 50 mL HDPE container add 50.0 mL of metal free water and 8.4 g of NaHCO3 and agitate to dissolve completely. (This yields a 2 M NaHCO3 solution). Mix 17.8 mL of 4M NaOH solution and 50 mL of 2M NaHCO3 solution in a Coning Costar 250 mL storage bottle (or equivalent). Mix well.

Alternatively:

1.0 M $NaHCO_3$. In a 100 mL HDPE container add 50.0 mL of metal free water and 8.4 g of $NaHCO_3$ and mix with 17.8 mL of 4M NaOH solution. Agitate until total dissolution and bring the volume to 100 mL. Keep the solution in a Coning Costar 250 mL storage bottle (or equivalent). Mix well.

0.1M HEPES solution. Place 3.0 mL of 1M HEPES buffer (Fisher BioReagents, product number BP299-500) in a 50 ml HDPE bottle and add 27 ml of water for injection.

2.3.2.2 Materials

TABLE 2

List of chemicals and materials for the conjugation

| chemical/material | Order name | Specifications/Composition | Supplier |
|---|---|---|---|
| HCl, 30% | 1.00318.1000 | Suprapure | VWR |
| NaOH, 30% | 1.05589.0250 | Suprapure | VWR |
| Na acetate | 1.062640050 | >99.99% | VWR |
| NH$_4$ acetate | 372331-1004030KH | >99.999% | Sigma Aldrich |
| Acetic acid Glacial, 100% | 100264 1000660250 | Suprapure | VW |
| DOTA-NHS-ester | B-280 | | Macro cyclics, Dallas, TX |
| DOTA-p-SCN-Bn | B-205 | | Macro cyclics, Dallas, TX |
| NaCl | 1.064060050 | >99.99% | VWR |
| Hum195 | | 5 mg/ml | Isotex |
| DTPA | 1083900250 | >99% | VWR |
| Metal free water | 1.01262.1000 | ultrapure | VWR |
| Na$_2$HPO4 | 106566.0050 | Suprapur 99.99 | VWR |
| NaH$_2$PO4 | 106370.0100 | Suprapur 99.99 | VWR |
| Disposable PD-10 Desalting column | 17-0851-01 | | GE Health Care Europe GmbH |
| pH paper | 1.09533.0001 1.09542.0001 | pH = 5.0-10 pH = 4.0-7 | VWR |
| PP Eppen dorf vials | 211-2130 | PP | VWR |
| Heating block | 460-3249 | 203 × 315 × 89 | VWR |
| PE vials | 6008117 | PE | Perkin Elmer GmbH |
| Protein Pack 300SW | WRT080013 | Protein Pack 300SW | Waters |
| Protein Pack 125 centriguard column | WRT1866000926 | Protein Pack 125 centriguard column | Waters |
| Na azide Na$_3$N | 8.22335.0111 | Pure ≥99% | VWR |
| HEPES | BP299-100 | | Fisher BioReagents |
| NaHCO$_3$ | 106329.0500 | | VWR |
| Pipettes Eppendorf | 613-3646 | 0.5-10 μL (grey tip) | VWR |
| | 613-3649 | 10-100 μL (yellow tip) | |
| | 613-3650 | 100-1000 (blue tip) | |
| Pipette tips Eppendorf | 612-1158 | 0.5-10 μL (grey tip) | VWR |
| | 612-1160 | 10-100 μL (yellow tip) | |
| | 612-1163 | 100-1000 (blue tip) | |
| Millipore centrifugal devices YM-10 | 4411 (for 8 units) 4421 (for 24 units) | With a filter cut off for molecular weight of 10 000 MW | Millipore |
| Nalgene Containers | 2002-0001 2002-0002 2002-0004 | 30, 60 and 125 mL for storage of solutions | VWR |
| Amicon Ultra Centrifugal Filter Device for less than 4 mL Ultra-10K, regenerated cellulose 10 000 MW cut off | Catalogue Number UFC801096 | | Millipore |

2.3.2.3 Instrumentation:

Ultracentrifuge with refrigeration (4° C.) "Biofuge primo R, Heraeus'" or equivalent from Themo Scientific or similar (spinning at 6500 rpm)

Vortex or Similar System

UV-Visible Spectrophotometer Varian Cary—Win 5000 equipped with computer for spectrum storage and evaluation or a similar system (or equivalent)

HPLC with UV detector and a Waters Protein Pack 300SW as stationary phase equipped with computer for spectrum storage and evaluation (or Equivalent)

Refrigerator (4-8° C.) store the mAb and conjugated mAb

Freezer (−20° C.) to store the BFC-DOTA,

Analytical balance

Heating block or Nutator inside an oven 2.3.3 Calibration of the HPLC—UV Detector for Quantification of HuM195. Quality Control of HuM195

2.3.3.1 From the 5 mg/mL solution of HuM195, prepare at least three diluted solutions containing known concentrations which are defined by the sensitivity of the radioactive detector coupled to the SE-HPLC and settings in use. Usually a range of concentrations of 125-625 μg/mL is adequate as sensitivity and linearity are concerned.

2.3.3.2 Set up the HPLC for the measurements using the UV detector at 280 nm.

2.3.3.3 Condition the SE-HPLC column in 0.9% NaCl using a speed of 0.5 mL/min.

2.3.3.4 Take aliquots from the diluted HuM-195 solutions (or from the conjugate) and pass them through a SE-HPLC/UV. For example, for an HPLC set up with an injection system of 100 μL-loop, the amount of protein through the Protein Pack 300SW column will range from 12.5 μg to 62.5 μg. As a mobile phase use 0.9% NaCl. See FIG. 2 as illustration of a typical chromatogram.

2.3.3.5 Establish the relationship between the signal Ic (area under the peak) and concentration. Generate the calibration curve (see FIG. 3 with shows typical chromatograms) to allow the analyst to calculate the concentration of Hum195 in a conjugate sample*. Another approximate approach is based on finding the ratio concentration/signal obtained from the SE-HPLC/UV chromatogram of a standard HuM-195 sample. If the condition of linearity is fulfilled, then the ratio of concentration/signal will be a constant, K280 nm. Thus the concentration of Hum-195 in a conjugate sample is calculated according to the formula below:

$$C(\text{HuM195, mg/mL}) = K_{280nm} * I_s * D_f$$

Figure 2:
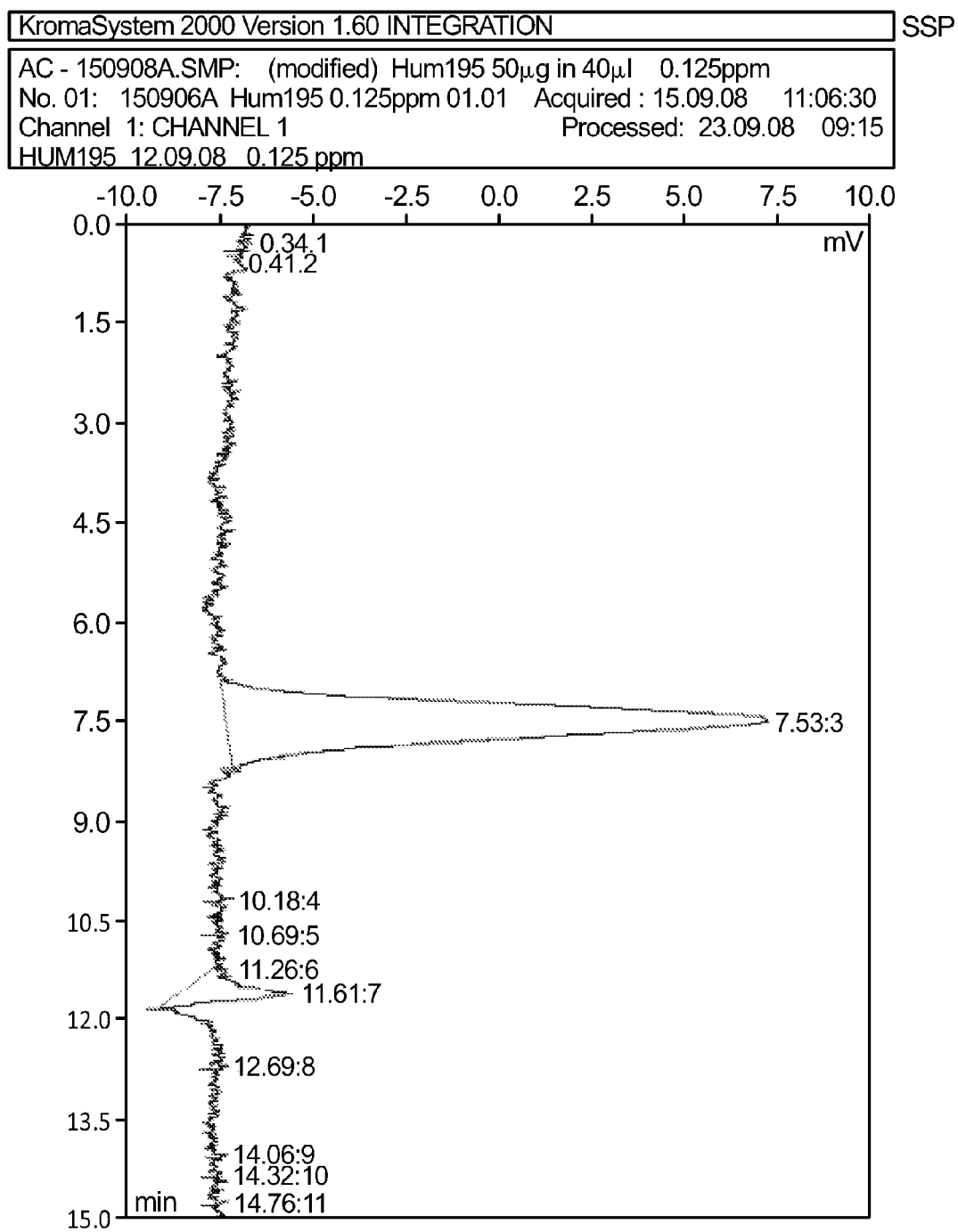
FIG. 2 SE—HPLC/UV chromatogram of the native Hum195.

$K_{280nm}$ Ratio of concentration of HuM195 (mg/mL) in the calibration sample to the Area ($I_c$) under the peak on the UV (set at 270 nm) chromatogram of the calibration sample $I_c$ Area under the peak on the SE-HPLC/UV (280 nm) chromatogram of the calibration sample (FIG. 2)

Figure 4:
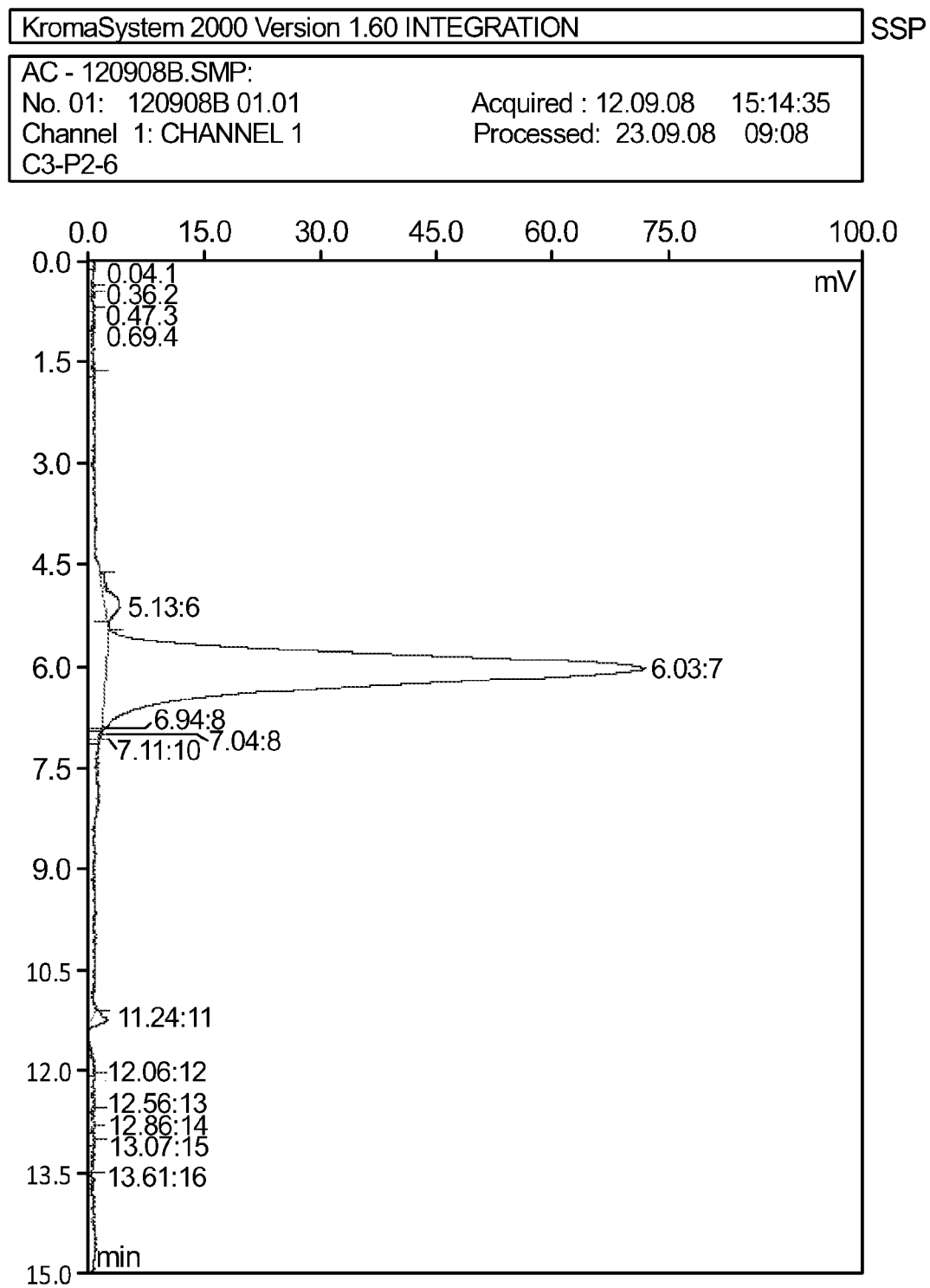
FIG. 4 SE—HPLC/UV chromatogram of the conjugate.

$I_s$ Area under the peak on the SE-HPLC/UV (280 nm) chromatogram of the sample (FIG. 4)

$D_f$ Dilution factor

C (HuM195, mg/mL) Concentration of HuM195 in the undiluted sample in mg/mL

Figure 1B:
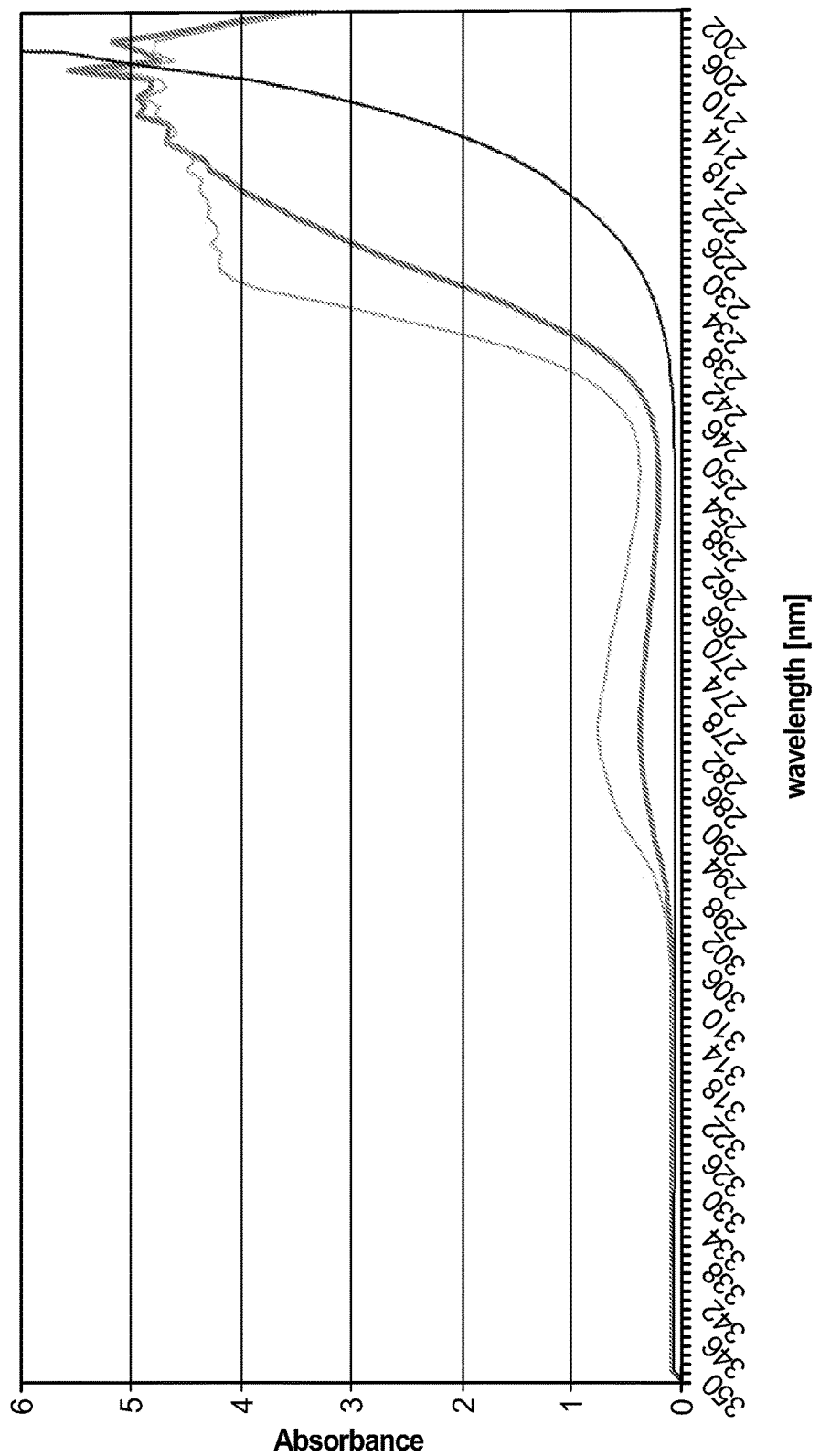
FIG. 1B UV—spectrum of HSA (0.1% in green), of native Hum-195 (100 µg/mL in pink) and of DTPA/NaAc (100 µg/mL)

* Conjugate solution should not contain free BFC or any other substance absorbing at 280 nm (See FIG. 1B)

2.3.4 Optional: Concentration of mAb by Filtration-Centrifugation

This step is relevant when large quantities of conjugates are to be prepared. The procedure below is applied to handling approximately 10 mg HuM-195 per single experiment/vial.

2.3.4.1 Take a new Millipore centrifugal device YM-10 with cut off for molecular weights 10 000 MW (YM devices of higher cutoff may be used with the corresponding increase in the spin time) and washed it with a few mLs of 0.05 M HCl and pure H2O.

2.3.4.2 Adjust in advance the temperature of the centrifuge tube to 4° C.

2.3.4.3 Weigh 2 mL of the native 5 mg/mL HuM195 solution or purified Hum195 and transfer it to the centrifugation tube.

2.3.4.4 Centrifuge the solution at 6500 rpm and 4° C. until the volume of the solution is 1 mL or less.

2.3.4.5 After centrifugation, turn the centrifugal tube and centrifuge again at 500 rpm to collect the concentrated mAb solution in the retentate vial.

2.3.4.6 Transfer the concentrated mAb (approximately 10 mg/mL) into an Eppendorf vial. Collect also the filtrate and analyse the content of HuM195 by SE-HPLC in both solutions. Keep the solutions at 4-8° C.

2.3.5 Conjugation Reaction in Bicarbonate Buffer 2.3.5.1 Thaw an Epperdonf vial containing 2.5 mg of DOTA/p-SCN-Bn in 0.25 mL metal free water.

2.3.5.2 Add 1 mL of a 5 mg/mL solution of HuM-195 (or 0.5 mL of 10 mg/ml) and mix the solution.

2.3.5.3 Add 0.05 mL of 1.0 M NaHCO3 and mix the solution 2.3.5.4 After mixing, check the pH by removing a 0.001 mL aliquot and spotting it on a pH paper with the proper pH range. The pH should be between 8 and 9, and target pH is 9. Continue to add 0.01 mL of 0.1M NaHCO3 and measure pH until the pH is between 8.0 and 9.2.

2.3.5.5 Incubate the reaction mixture in the nutator at 37° C. for 1 hour and 30 minutes 2.3.6 Optional: Conjugation Reaction in Phosphate Buffer 2.3.6.1 Weigh 5 mg of /p-SCN-Bn-DOTA in a previously cleaned Eppendorf vial and dissolve it in 0.4 mL 0.1M phosphate buffer pH=8.

2.3.6.2 Mix gently the concentrated mAb solution of approximately 10 mg/mL with the 400 μL of phosphate buffer solution.

2.3.6.3 After mixing, check the pH by removing a 0.001 mL aliquot and spotting it on a pH paper with the proper pH range. The pH should be between 8.0 and 9.2.

2.3.6.4 If the pH is too low add 0.010 mL aliquots of 2 M NaOH to the solution and mix gently the solution.

2.3.6.5 Repeats steps 2.3.6.3 and 2.3.6.4 until target pH is reached. Approximately, 0.03 mL 2 M NaOH solution are needed to reach the target pH.

2.3.6.6 Close the Eppendorf vial and use a Vortex system for mixing, let it for 24 hours at room temperature or proceed as described in the following step 2.3.6.7.

2.3.6.7 Alternately incubate the reaction mixture in the heating block or in the incubation shaker cabinet at 37° C. for 1 hour and 30 minutes.

2.3.7 Purification of the Reaction Mixture by Filtration-Centrifugation. QC for SE-HPLC/UV 2.3.7.1 Transfer the entire construct reaction mixture (sections 2.3.5.5 or 2.3.6.7) into a new Millipore centrifugal device YM-10 or equivalent (10 000 MW cut off) Filters of 20,000 or 40,000 molecular weight cut off are also acceptable.

2.3.7.2 Add 1 mL of 0.1M HEPES or 0.1 M NaAc and centrifuge the sample at 6500* rpm and 4° C. until the volume of the solution is about 1 mL. * Lower spin can be used with consequent increase in the separation time. Use manufacturer instructions when using other filters.

2.3.7.3 Repeat step 2.3.7.2 three more times.

2.3.7.4 Take a small aliquot from the final purified conjugated fraction and pass it through a SE-HPLC consisting of a Protein Pack 300SW column (refer to 2.3.3). As a mobile phase use 0.9% NaCl. Compare with non-conjugated MAb, the conjugated MAb shows a peak shifted to the left on the chromatogram (see FIG. 4).

2.3.7.5 Analyse the SE-HPLC/UV chromatogram (see ex. FIG. 4) and check that no signal region corresponding to free BFC is observed.

2.3.7.6 If free BFC is observed on the SE-HPLC/UV chromatogram, then repeat step 2.3.7.2 otherwise continue with the following step.

2.3.7.7 Quantify the content of conjugated mAb in the sample as described in 2.3.3.4-2.3.3.5 for the calibration experiment or as indicated in section 2.3.9.

2.3.7.8 Store the purified conjugated fraction at 4-8° C.: the sample is ready for radiolabeling.

2.3.8 Optional: Purification of the Reaction Mixture by Gravity SE-Chromatography and Filtration-Centrifugation.

The procedure below is an alternative to the method described in 2.3.7.

2.3.8.1 See step 2.3.7.1.

2.3.8.2 Condition a new PD-10 resin in 0.1 M NaAc solution by passing through the column 5 mL 0.1 M NaAc. Discard the washings.

2.3.8.3 Apply the entire construct reaction mixture (after sections 2.3.6.7 or 2.3.5.5) to the reservoir of the column and collect the eluate in Eppendorf tubes or PE vials (fraction 1).

2.3.8.4 Wash the reaction vial with 0.5 mL 0.1 M NaAc solution and pour the washings into the reservoir of the PD-10 column.

2.3.8.5 Collect the eluate in an Eppendorf tube separately (fraction 2).

2.3.8.6 Repeat steps 2.3.8.4-2.3.8.5 two times (fractions 3, 4).

2.3.8.7 Continue applying 0.5 mL 0.1 M NaAc into the reservoir of the PD—10 column and repeat this operation until a total elution volume of 6 mL is reached (fractions 5, 6, 7, 8, 9, 10, 11, 12).

2.3.8.8 Wash the column two more times each with 2 mL 0.1 M NaAc (fractions 13 and 14). Collect the eluents.

2.3.8.9 Combine fractions 5 to 12 (4 mL) as these contain most of the conjugated mAb. Fractions 13 to 14 contain most of the unbound or free BFC.

2.3.8.10 Proceed as indicated in steps 2.3.7.2-2.3.7.8.

2.3.9 Determination of Protein Concentration by UV-Spectrophotometry in the Conjugate 2.3.9.1 Set the UV spectrophotometer at 280 nm (to see a typical UV spectrum of native and conjugated Hum-195 refer to FIG. 1).

Figure 5:
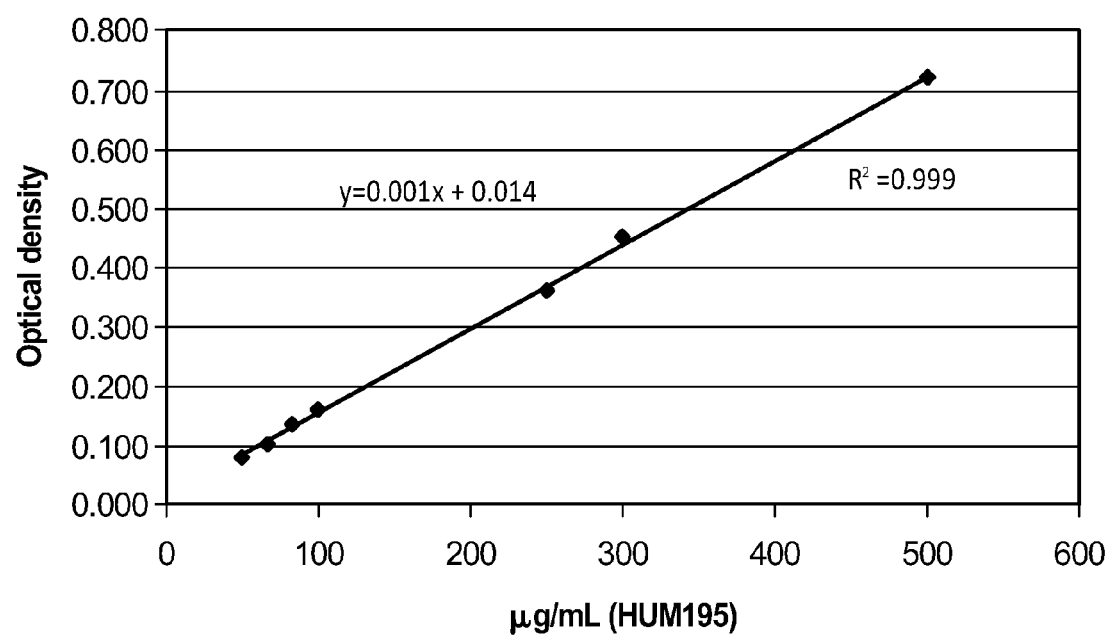
FIG. 5 Typical calibration curve, wavelength=280 nm for calibration of the UV spectrophotometer in the quantification of HuM-195.

2.3.9.2 Prepare one dilute standard sample or optionally, to generate a calibration curve, at least three diluted standard solutions with known HuM195 concentrations in 0.9% NaCl and find the region of linearity between the optical density (typically 0.1-0.8) and concentration (typically 60-600 600 µg/mL). Refer to FIG. 5 for an example of a calibration curve. For HuM195 solutions at 0.1% (1 mg/mL in 0.9% NaCl) in 1 cm—optical path cuvette the absorbance is approximately 1.4.

2.3.9.3 Calculate the protein concentration in the sample either by using the calibration curve from the graph "optical density vs. concentration" (e.g. in FIG. 5) or less accurately based on the following equation:

$$C(\text{HuM195}, \text{mg/mL}) = A_{280nm} * D_f * f_c / \epsilon_{280nm} \cdot L$$

$A_{280nm}$ Absorbance at 280 nm
$\epsilon_{280nm}$ Extinction coefficient at 280 nm for 0.1%=1.4
L cuvette's optical path, 1 cm
$D_f$ Dilution factor
$f_c$ Factor which corrects for the difference in the extinction coefficients of the native and conjugated IgG. This factor is approximately 1 at 280 nm (refer to FIG. 1)
C(HuM195 conj, mg/mL) Concentration of HuM-195 in the undiluted sample in mg/mL Example 3

Description of the Radiolabeling Procedure: One Step Method 3.1 Scope
To label 225Ac with HuM-195 previously conjugated with DOTA bifunctional chelating agents.

3.2 Nomenclature and Definitions
See also example 1.
DTPA: Diethylentriaminpentaacetic acid
Gentisic acid: 2,5 Dihydroxibenzoic acid
AA: Ascorbic acid 3.3 Radiolabeling Protocol
3.3.1 Materials and Chemicals
See Table 3

TABLE 3

List of chemicals and materials for the labelling

| chemical/material | Order name | Specifications Composition | Supplier |
|---|---|---|---|
| 30% HCl | 1.00318.1000 | Suprapure | VW |
| NaOH, 30% | 1.05589.0250 | Suprapure | VW |
| Na acetate | 1.062640050 | >99.99% | VW |
| NH4 acetate | 372331-10904030KH | >99.999% | Aldrich |
| Acetic acid | 100264 | Suprapure | VW |
| Gentesic acid | 841745 | >99% | VW |
| Ascorbic acid for biological applications | 101566.0100 | >99% | VW |
| DOTA-NHS-ester | B-280 | | Macro cyclics, Dallas, TX |
| DOTA-p-SCN-Bn | B-205 | | Macro cyclics, Dallas, TX |
| NaCl | 1.064060050 | >99.99% | VW |
| HuM195 | | 5 mg/ml | PDL/Pacific GMP |
| DTPA | 1083900250 | >99% | VW |
| Metal free water | 1.01262.1000 | ultrapure | VW |
| Disposable PD-10 Desalting column | 17-0851-01 | | GE Health Care Europe GmbH |
| pH paper | 1.09543.0001 | pH = 6.5-10 | VW |
| | 1.09542.0001 | pH = 4.0-7 | |
| PP Eppen dorf vials | 211-2130 | PP | VW |
| | 211-2160 | | |
| Heating block | 460-3249 | 203 × 315 × 89 | VW |
| PE vials | 6008117 | PE | Perkin Elmer GmbH |
| Protein Pack 300SW | WRT080013 | Protein Pack 300SW | Waters |
| Protein Pack 125 centriguard column | WRT1866000926 | Protein Pack 125 centriguard column | Waters |
| filters | 514-7014 | 0.45 µm pore size 25 mm diameter | VW |
| Pipettes Eppendorf | 613-3646 | 0.5-10 µL (grey tip) | VW |
| | 613-3649 | 10-100 µL (yellow tip) | |
| | 613-3650 | 100-1000 (blue tip) | |

TABLE 3-continued

List of chemicals and materials for the labelling

| chemical/material | Order name | Specifications Composition | Supplier |
|---|---|---|---|
| Pipette tips Eppendorf | 612-1158 612-1160 612-1163 | 0.5-10 µL (grey tip) 10-100 µL (yellow tip) 100-1000 (blue tip) | VW |
| ITLC SG 5 × 20 cm | 516-7805 | | VW |
| Human serum albumina (HSA) - - - | PZN-0504775 | 1% 20% | Swiss Red Cross, Bern, Switz. Behring |
| Sterile tubes, pipette tips, plasticware | | | |
| 50 mL Corning tubes | | | Sigma-Aldrich |
| Nunc tubes | | | Sigma-Aldrich |
| 10DG size exclusion desalting columns | 732-2010 | MW cut off 6000 | Biorad Inc. |

3.3.2 Preparation of Chemicals and Conditions for the Reaction

Reaction Vial and Heating Block 3.3.2.1 Take a new reaction tube (e.g. 2 mL capacity Eppendorf tube) and wash it with a few mLs of 0.1 M HCl, water for injection H2O and finally with the 0.5 M NaAc (0.5 M NH4Ac) buffer.

3.3.2.2 Calibrate the heating block using the same type of reaction tube as for the labelling. The temperature in the liquid (water) inside the tube should be 37±2° C.

Preparation of the Ac-225

3.3.2.3 Quantify the activity of 225Ac in the vial obtained from the manufacturer.

3.3.2.4 Dissolve the residue in the vial (if the sample is dried) in 0.05 mL of a 0.2M HCl solution. For radiolabeling, the aliquot taken should be less than 0.3 mL.

3.3.2.5 Inspect for the presence of insoluble material. The residue should be completely dissolved and the resultant solution should be homogeneous, transparent and free of particles and foreign material.

Other Chemical and Materials 3.3.2.6 For the labelling, prepare in advance the following solutions:

p-SCN-Bn-DOTA-mAb conjugate solution of protein concentration in the 5-10 mg/mL in 0.9% NaCl as described in section 2

0.5 M NH4Ac (or NaAc): Take 4.2 mL of the 3 M NaAc and mix with free metal water bring the volume to 25 mL. Mix the solution and after homogenization filter it through a 0.45 µm cellulose acetate membrane filter. Keep the solution in a 25 mL-HDPE container Solution of gentisic acid in 3 M NaAc: Weigh 0.033 g of gentisic acid in dissolve in 1 mL 3 M NaAc. Before use, filter the solution through a 0.45 µm cellulose acetate membrane filter. Keep the solution in a 2 mL—capacity Eppendorf vial in cool and darkness.

150 g/L l-AA solution: Weigh 1.5 g of AA and dissolve in 10 mL free metal water. Filter the solution through a 0.45 µm cellulose acetate membrane filter. Keep the solution in a 25 mL-HDPE container in cool and darkness.

50 mM DTPA solution: Weigh 0.49 g of DTPA and dissolve in 25 mL free metal water. Filter the solution through a 0.45 µm cellulose acetate membrane filter. Keep the solution in a 25 mL-HDPE container 20 mM DTPA solution: Weigh 0.20 g of DTPA and dissolve in 25 mL free metal water. Filter the solution through a 0.45 µm cellulose acetate membrane filter. Keep the solution in a 25 mL-HDPE container Prepare the following materials PD—10 column pH papers: thin strips of pH paper in the range 4-10

Eppendorf vials

PE vials 0.45 µm 25 mm-diameter Cellulose acetate filters and sterile syringes for filtration ITLC SG 5×20 cm 3.3.2.7 Filter through 0.45 µm 25 mm Cellulose acetate filters the non-radioactive solutions before labelling 3.3.2.8 Instrumentation:

Vortex or similar system

HPLC with UV detector and a Protein Pack 300SW SEC column as stationary phase

Refrigerator (4-8° C.) to store the mAb and conjugated mAb samples

Freezer (−20° C.) to store the BFCs

Gamma-spectrometry system with a high purity Germanium detector. Optionally and particularly for activity balance assessments, the detector should be also ISOCS characterized by Can berra Industries and with the ISOCS/LABSOCS software package which runs under the standard GENIE 2000 software configuration to enable absolute measurements for each specific counting geometry e.g. vial, columns, etc.

Squibb CRC-17 Radioisotope Dose Calibrator (or equivalent model)

3.3.3 Radiolabeling 3.3.3.1 Take an aliquot of not more than 0.3 mL 0.05 M HCl which contains the required activity of 225Ac (e.g. app. 1 mCi on the labelling day) and pipette it into the reaction tube (update table in section 3.3.7.3).

3.3.3.2 Optionally, measure the activity of 225Ac in the reaction tube by high resolution gamma-spectrometry.

3.3.3.3 Add 0.1 mL 3M NaAc (or NH4Ac) and mix gently and shortly using a Vortex system.

3.3.3.4 Check the pH by removing a 0.001 mL aliquot and spotting it on a pH paper with the proper pH range. The pH should be between 5 and 8.5. Do not discard the tip and pH paper: collect them in small PE bag for radioactivity balance assessment.

3.3.3.5 Depending on the concentration of HuM195 in the conjugate solution, add 0.1 mL (when 10 mg/mL) or the calculated volume of the p-SCN-Bn-DOTA-mAb conjugate solution which contains app. 1 mg of mAb. The volume should not exceed 0.2 mL.

Remark: In the control experiment, this step is omitted.

3.3.3.6 Add 0.020 mL of a fresh prepared saturated gentisic acid solution and mix shortly and gently using a Vortex system.

3.3.3.7 Repeat 3.3.3.4. The target pH should be between 5.5-7.0.

3.3.3.8 If the pH is above 7.0, add 0.010 mL of 0.1 M HCl. If the pH is below 5.5, add 0.025 mL of 3 M NaAc.

3.3.3.9 Repeat step 3.3.3.8, if necessary.

3.3.3.10 Close the 2 mL reaction vial reaction tube containing the reaction mixture and place it into the heating block (3.3.2.2) at 37° C. for 80-90 minutes 3.3.4 DTPA Challenge and Determination of the Reaction Yield by ITLC 3.3.4.1 After 90 minutes, stop the reaction and add 0.010 mL of a 10 mM DTPA solution and mix shortly and gently using a Vortex system.

3.3.4.2 Place the reaction tube back in the heating block and incubate for 30 minutes.

3.3.4.3 After 20 minutes, switch off the heating block, remove from the reaction mixture a 0.002 mL aliquot and spot it on the centre of the reference line of the ITLC stripe (a line marked at approximately 15 mm from one side). Collect the empty tip in the bag for wastes (see 3.3.3.4). Keep safe the tube containing the reaction mixture.

3.3.4.4 Place the ITLC in a glass tube containing the mobile phase: a few mL of a 20 mM DTPA solution (depending on the size of the container used for ITLC.

3.3.4.5 Wait 7-8 minutes until the mobile phase front reaches the second reference line marked at approximately 15 mm from the other end of the stripe.

3.3.4.6 Remove the strip from the ITLC tube and let it dry. Then cut the stripe in small sections, each one at the distance of 15 mm.

3.3.4.7 Place each section in previously numerated polyethylene vials (e.g. 20 mL PE vials normally used for liquid scintillation counting).

3.3.4.8 Wait 1 hour and count the activity of 225Ac by measuring the 221Fr on a high resolution gamma spectrometer in each chromatogram section for first evaluation (Optional).

3.3.4.9 Wait more than 6 hours for radioactive equilibrium between 225Ac and all daughters and measure the activity of 225Ac through both 221Fr and 213Bi for final evaluation.

3.3.4.10 Calculate the radiolabelling yield by using the following formula:

$$Y(\%) = (A_1 + A_2) * 100\% / A_t$$

Where,
Y=radiolabeling yield in %
$A_1$=activity of $^{225}$Ac measured in section 1 of the chromatogram (numerated from the bottom), Bq (μCi)
$A_2$=activity of $^{225}$Ac measured in section 2 of the chromatogram, Bq (μCi)
$A_t$=summa of $^{225}$Ac activity measured in all sections of the chromatogram, Bq (μCi)

If the samples are measured using the same geometry (source to detector distance, same vials, detector, etc) then the yield can be calculated using the following formula:

$$Y(\%) = (I_1 + I_2) * 100\% / I_t$$

Where,
Y=radiochemical yield in %
$I_1$=count rate of $^{225}$Ac measured in section 1 of the chromatogram (numerated from the bottom), cps
$I_2$=count rate of $^{225}$Ac measured in section 2 of the chromatogram, cps
$I_t$=count rate of $^{225}$Ac measured in all sections of the chromatogram, cps 3.3.5 Purification of the Reaction Mixture by Size Exclusion Chromatography Using the 10DG Column 3.3.5.1 Obtain the following components: 10 mL of 10 DG SE resin; column components, and 3-way stopcock for the purification steps described below.

3.3.5.2 Pour the 10 mL volume of 10 DG resin into plastic disposable column, allow to settle and apply the top frit. All these materials are obtained from Biorad Inc., Hercules Calif. Wash the packed resin with two 10 mL volumes of 0.9% NaCl. Discard the washes.

3.3.5.3 Equilibrate the resin with two 10 mL volumes of 1% HSA. Discard the washes.

3.3.5.4 Tare a new 50 mL sterile Corning tube for collection of the drug product and apply the entire construct reaction mixture (refer to 3.3.4) to the column and collect the eluent in a waste tube.

3.3.5.5 Wash the construct reaction vial with 0.20 mL 1% HSA and add this wash to column and again collect the eluate in a waste tube. Add 2.0 mL of 1% HSA as a mobile phase and again collect the eluate in a waste tube. Add 2 mL of 1% HSA to the size exclusion column and collect the final product.

3.3.5.5 Weigh the drug product collected and record the mass of solution containing the product.

3.3.5.6 Assume that 80% of the 1.0 mg of antibody has been recovered using the purification scheme. Calculate the specific activity of the product by dividing the activity by the total amount of HuM195 recovered (0.8 mg). The activity level of the product can be determined after a 6 hour period following the purification. This time is required for Ac-225 secular equilibrium to be established and measured in a dose calibrator or equivalent to determine the product yield and activity level 3.3.6 Optional: Purification of the Reaction Mixture by Size Exclusion Chromatography Using a PD-10 Column This is an alternative to the procedure described in section 3.3.5

3.3.6.1 Condition the PD-10 resin in 0.9% NaCl solution by passing through the column 5 mL NaCl 0.9%. Discard the washings.

3.3.6.2 Apply the entire construct reaction mixture (section 3.3.4.3) to the reservoir of the column and collect the eluate (fl) in Eppendorf tubes or PE vials.

3.3.6.3 Wash the reaction vial with 0.5 mL 0.9% NaCl solution and pour the washings into the reservoir of the PD-10 column. Place the empty reaction vial in a small PE bag for wastes for activity balance assessment (see 3.3.3.4)

3.3.6.4 Collect the eluate in Eppendorf tubes or PE vials separately.

3.3.6.5 Repeat steps 3.3.6.3-3.3.6.4 two times and collect these eluates together (fw).

3.3.6.6 Continue applying 0.5 mL 0.9% NaCl into the reservoir of the PD-10 column until a total elution volume of 6 mL is reached. Collect the eluates of 4 mL together. These fractions should contain most of the labelled conjugate (fp).

3.3.6.7 Wash the column with additional 8 mL 0.9% NaCl. Collect the eluate separately in a new container. This is the fraction which contains the free or associated with DTPA Ac-225 (ff).

3.3.6.8 Wait one (1) hour and count the activity of 225Ac by measuring the 221Fr on a high resolution gamma spectrometer in each vial for first evaluation (Optional).

3.3.6.9 Wait more than 6 hours for radioactive equilibrium between 225Ac and all daughters and measure the activity of 225Ac through both 221Fr and 213Bi for final evaluation.

3.3.6.10 If concentration is required, transfer the fraction $f_p$ (4 mL) into a new Millipore centrifugal device YM-10 with cut off for molecular weights 10 000 MW (YM tubes with membranes of higher cut-off may be used with the corresponding increase in the spin time). Otherwise go directly to 3.3.5.5.

3.3.6.11 Centrifuge the conjugate combined solution at 6500 rpm and 4° C. until the volume of the solution is approximately 1 mL.

3.3.6.12 Add 1 mol of 0.9% NaCl and repeat step 3.3.6.11.

3.3.6.13 Tare a new 50 mol sterile Corning tube for collection of the product.

3.3.6.14 Transfer the product to the new 50 mL sterile Corning tube.

3.3.6.15 Wash the empty YM—10 tube with up to 1 mL 1% HSA and transfer the washes to the tube containing the product.

3.3.6.16 Proceed as indicated in 3.3.5.5

3.3.7 Optional: Assessment of the Activity Balance 3.3.7.1 Measure the PD-10 column on a high resolution gamma spectrometer to quantify the activity of 225Ac left on the column.

3.3.7.2 Measure the bag containing the empty reaction vial, tips, and pH paper used for QC during the labelling experiment.

3.3.7.3 Summarize the results in the table below (Table 4):

| Compartment | Activity of $^{225}$Ac, mCi | % of activity |
|---|---|---|
| Initial activity of Ac-225 | | |
| In purified/concentrated fraction associated with mAb | | Recovery |
| In other liquid fractions not associated with mAb | | |
| Left on the PD-10 column | | |
| Left in reaction vial, tips, pH paper for QC, tissues, etc | | |

3.4 Quality Control of the Radiolabeled Conjugate 3.4.1 Appearance/Visual Test:

3.4.1.1 Visually inspect the product using a white and black background for clarity, color and absence of foreign matter.

Figure 9:
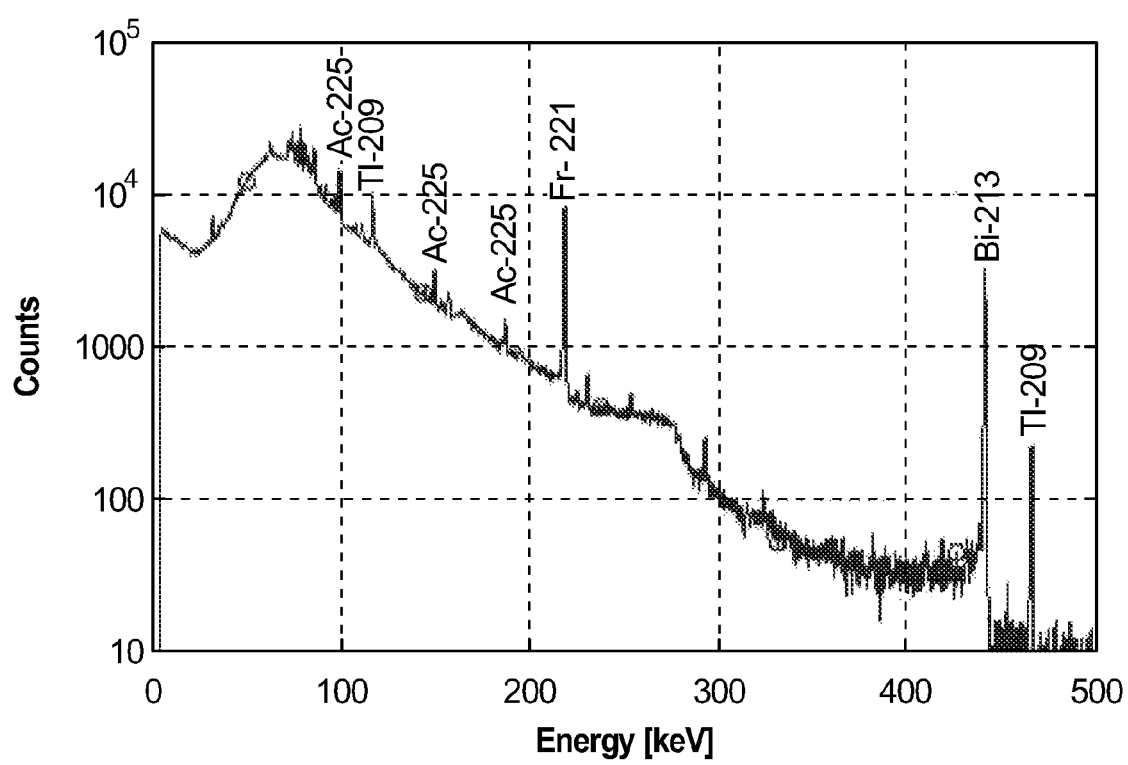
FIG. 9 Typical gamma-spectrum of Ac-225 and daughters on a high resolution Ge detector.
Figure 10:
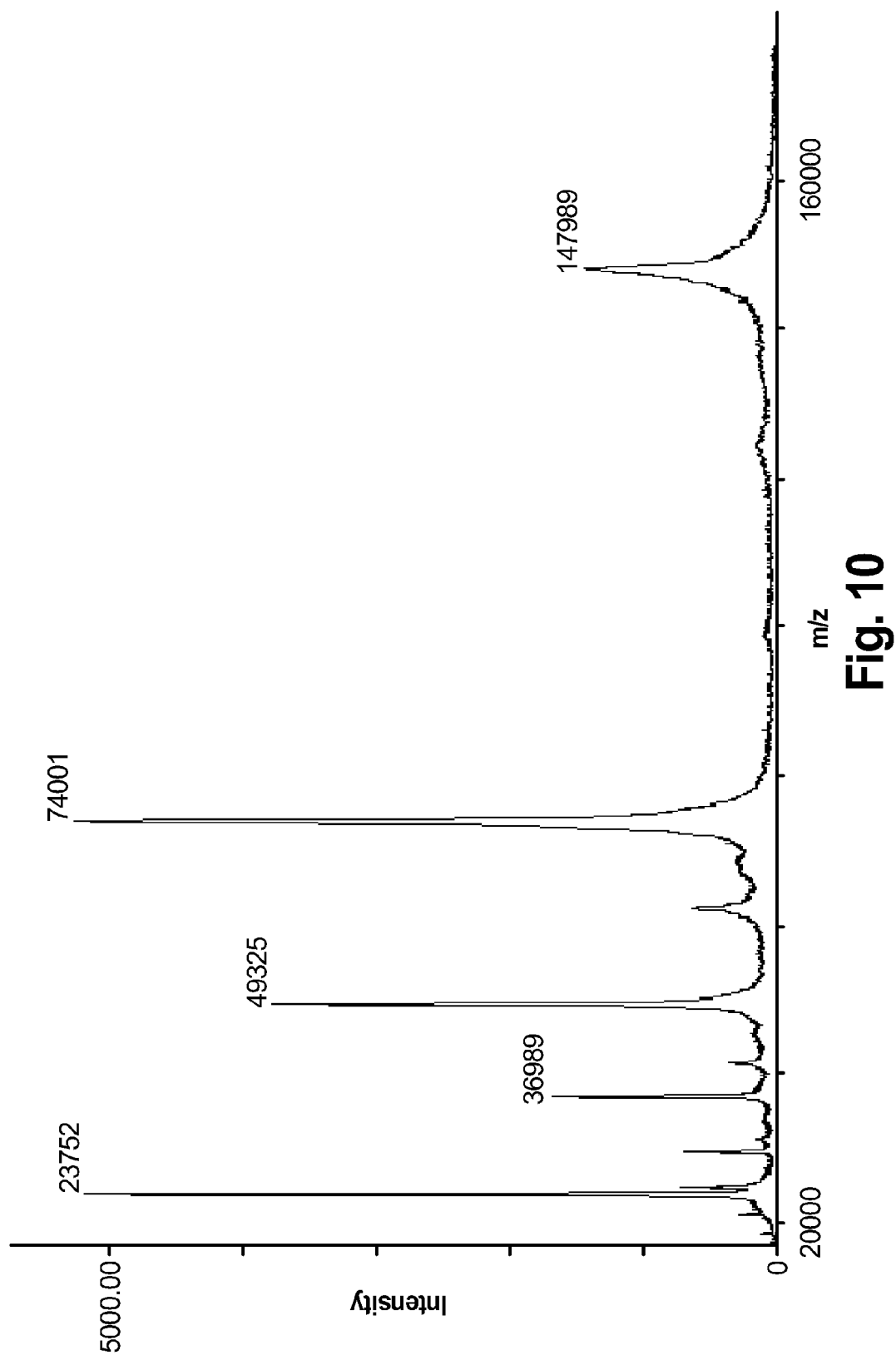
FIG. 10 Typical MALDI spectrum of native Hum195 with CHCA as matrix solution.
Figure 11:
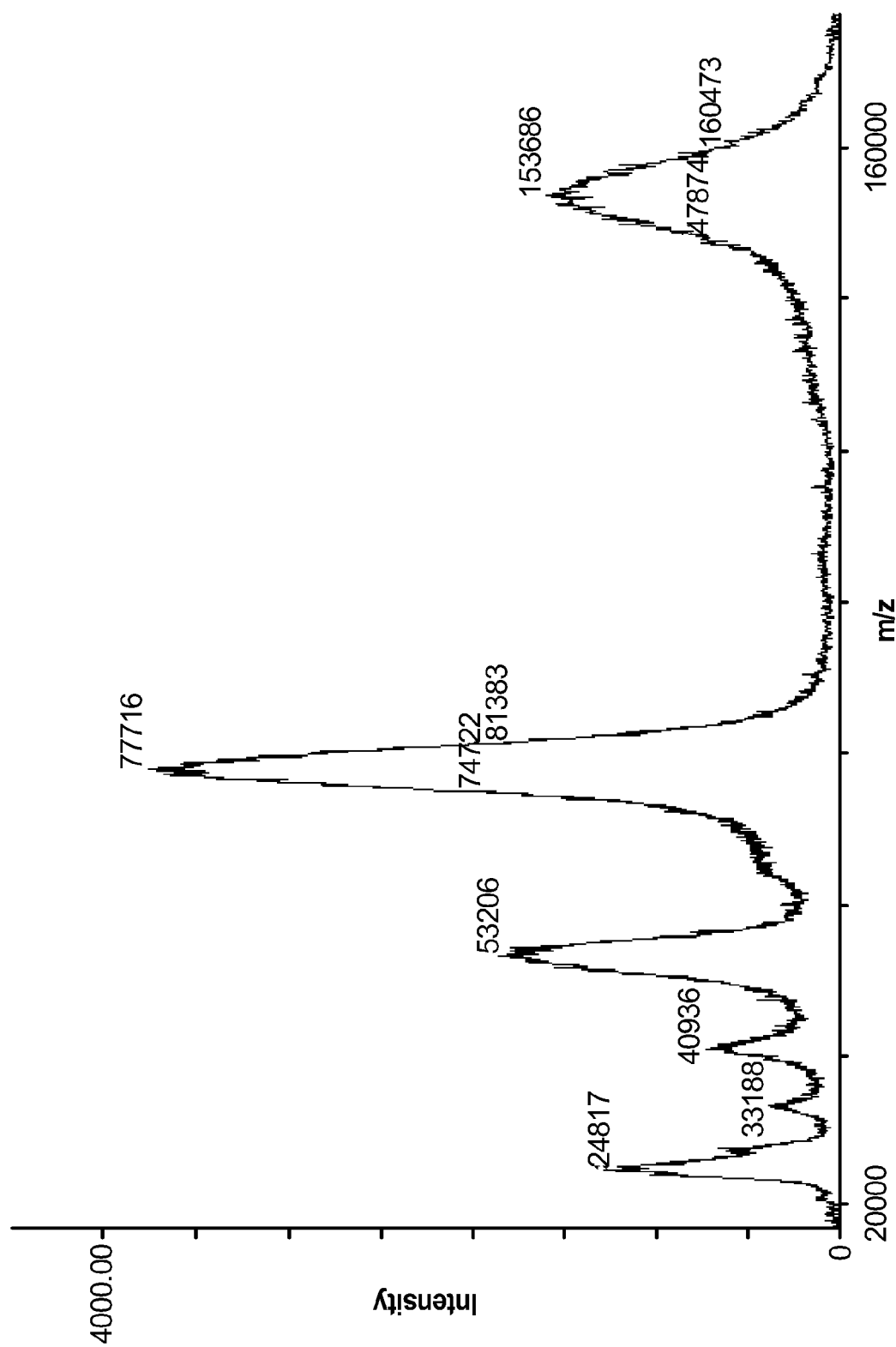
FIG. 11 Typical MALDI spectrum of conjugate with CHCA as matrix solution.
Figure 12:
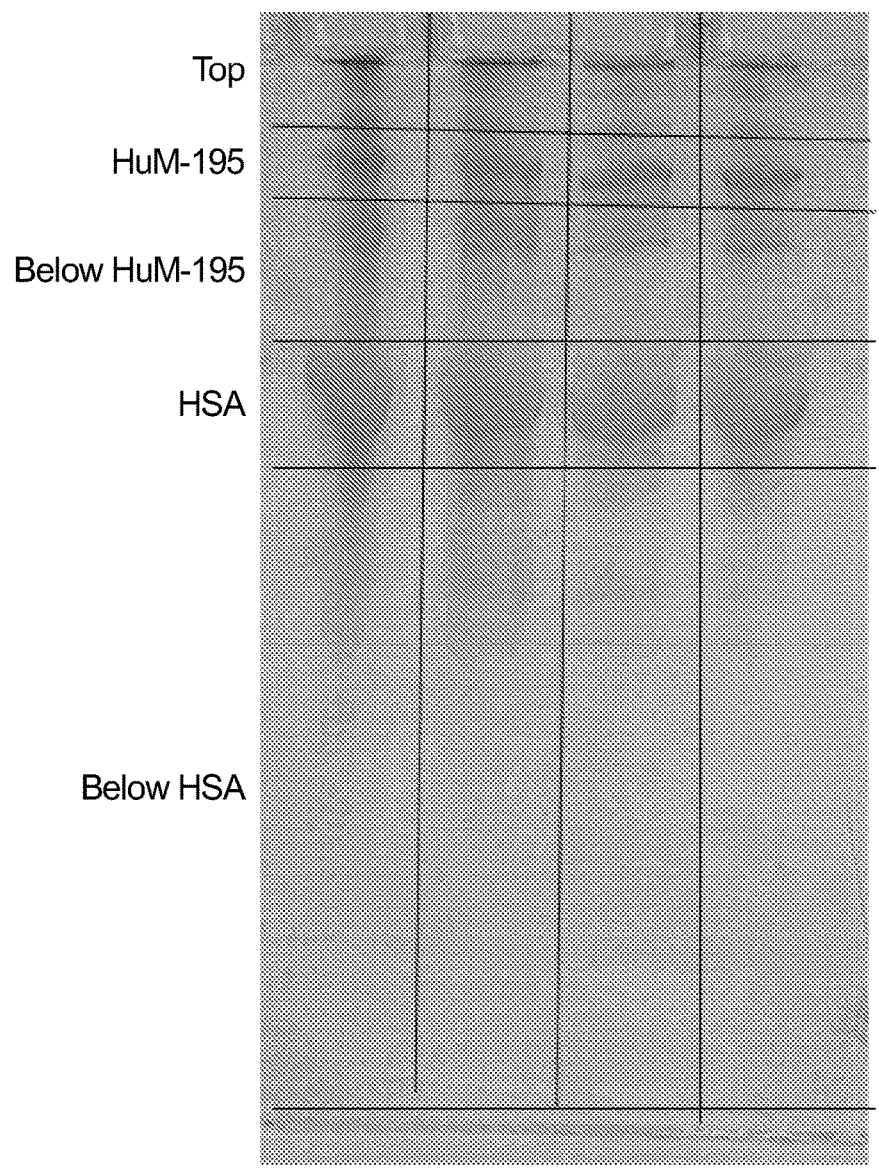
FIG. 12 PAGE Gel Electrophoresis of one step and two step preparations showing section of the gel that were cut for analysis of counts.
Figure 13:
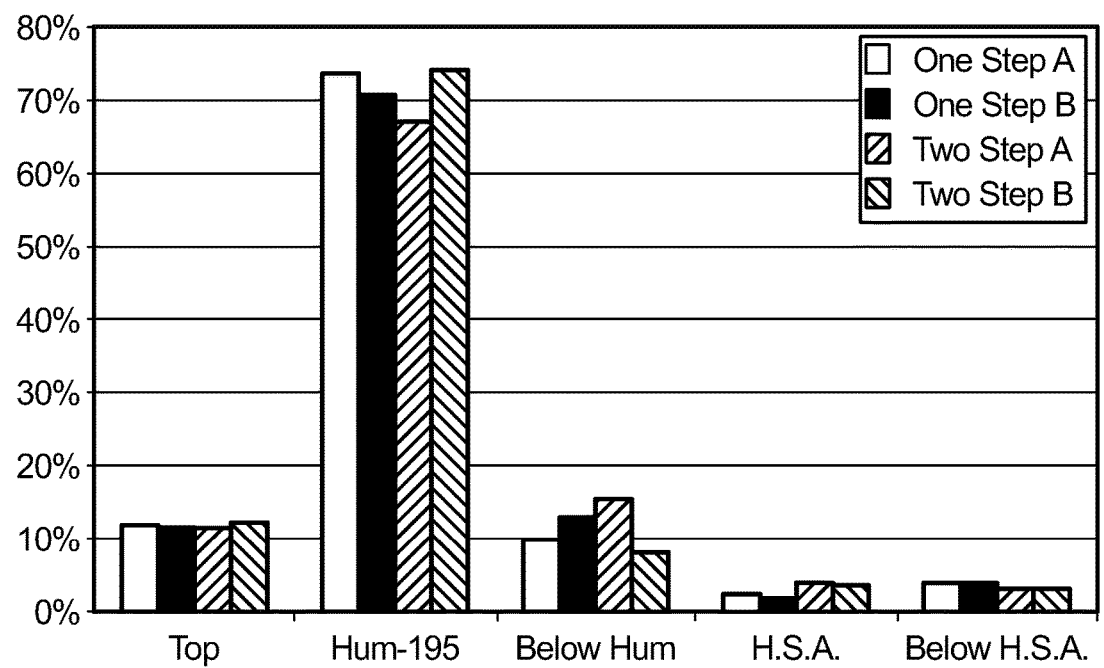
FIG. 13 Activity in each cut section of gel. Result are consistent with a significant percentage of the Ac-225 associated with HuM-195. Results were identical for one step and two step formulations.
Figure 14:
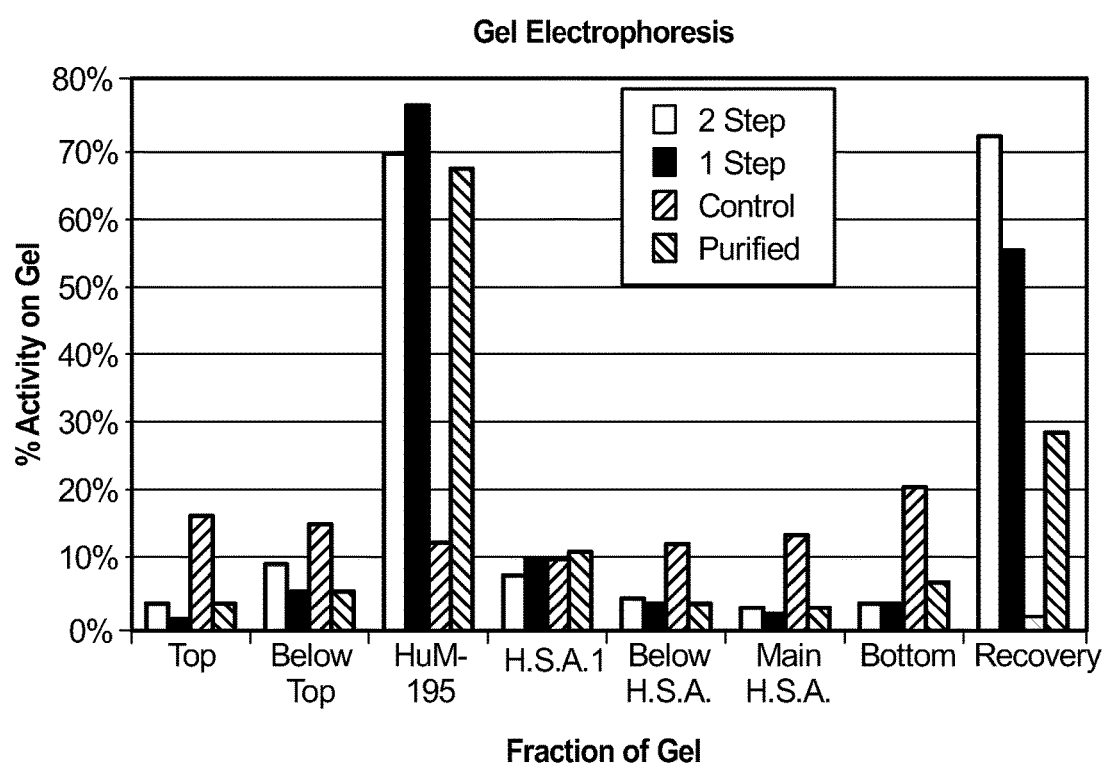
FIG. 14 PAGE Gel Electrophoresis was used to analyze a preparation using the one step process and a control. Control was prepared the same way as the one step procedure but the antibody was not conjugated with a DOTA bifunctional chelating agent prior to chelation with Ac-225. Control preparation shows very small amounts of Ac-225 associated with HuM-195 in contrast to the one step preparation.

3.4.2 Radionuclide Identification 3.4.2.1 Collect the gamma spectrum on a calibrated gamma spectrometer. Refer to FIG. 9 as example.

3.4.2.2 Using a standard nuclide library (see Table 1) look for the presence of main peaks at 218 keV from Fr-221 and 441 KeV from Bi-213. Look also for confirming peaks of Ac-225 and Tl-209.

TABLE 1

Nuclide Library*: Ac-225 and daughters

```
Library Listing Report         26.03.2009 15:22:20              Page 1

***********************************************************************
*****                    LIBRARY LISTING REPORT                   *****
***********************************************************************

Filename: C:/GENIE2K/CAMFILES/Ac.NLB
          Nuclide Library Description:
```

| Nuclide Name | Half-Life (Seconds) | Energy (keV) | Energy Uncert. (keV) | Yield (%) | Yield Uncert. (Abs.+−) |
|---|---|---|---|---|---|
| TL-209 | 8.640E+005 | 72.800 | 0.000 | 5.9100 | 0.0000 |
| | | 74.970 | 0.000 | 9.9800 | 0.0000 |
| | | 84.800 | 0.000 | 3.4000 | 0.0000 |
| | | 87.300 | 0.000 | 1.0000 | 0.0000 |
| | | 117.000 | 0.000 | 77.0000 | 0.0000 |
| | | 465.000* | 0.000 | 96.6000 | 0.0000 |
| | | 1566.000 | 0.000 | 99.7000 | 0.0000 |
| BI-213 | 8.640E+005 | 76.862 | 0.005 | 1.1800 | 0.0600 |
| | | 79.290 | 0.005 | 2.0000 | 0.1000 |
| | | 89.600 | 0.000 | 0.7000 | 0.0500 |
| | | 92.400 | 0.100 | 0.2000 | 0.0700 |
| | | 292.300 | 0.100 | 0.4960 | 0.0700 |
| | | 309.000 | 0.100 | 0.2000 | 0.0700 |
| | | 323.600 | 0.100 | 0.1360 | 0.0700 |
| | | 440.200* | 0.020 | 27.3000 | 1.2000 |
| | | 806.600 | 0.040 | 0.3500 | 0.0200 |
| | | 1101.000 | 0.060 | 0.3900 | 0.0230 |
| FR-221 | 8.640E+005 | 62.800 | 0.010 | 0.8000 | 0.1200 |
| | | 68.000 | 0.010 | 0.4000 | 0.1200 |
| | | 78.950 | 0.010 | 0.2000 | 0.1200 |
| | | 81.520 | 0.010 | 0.3000 | 0.2000 |
| | | 92.100 | 0.000 | 0.1000 | 0.0900 |
| | | 99.500 | 0.200 | 0.1400 | 0.0400 |
| | | 217.600* | 0.040 | 12.5000 | 0.9000 |
| | | 409.500 | 0.000 | 0.1260 | 0.0400 |

TABLE 1-continued

Nuclide Library*: Ac-225 and daughters

```
Library Listing Report        26.03.2009 15:22:20                    Page 1

************************************************************************
*****                    LIBRARY LISTING REPORT                     *****
************************************************************************

Filename: C:/GENIE2K/CAMFILES/Ac.NLB
        Nuclide Library Description:
```

| Nuclide Name | Half-Life (Seconds) | Energy (keV) | Energy Uncert. (keV) | Yield (%) | Yield Uncert. (Abs.+−) |
|---|---|---|---|---|---|
| AC-225 | 8.640E+005 | 62.900 | 0.030 | 0.5100 | 0.0220 |
|  |  | 73.700 | 0.020 | 0.5200 | 0.0150 |
|  |  | 83.200 | 0.020 | 1.5900 | 0.0700 |
|  |  | 86.110 | 0.020 | 2.5400 | 0.1200 |
|  |  | 87.300 | 0.030 | 0.3000 | 0.0120 |
|  |  | 97.300 | 0.000 | 0.9400 | 0.0600 |
|  |  | 99.600 | 0.050 | 2.9000 | 0.0400 |
|  |  | 100.300 | 0.050 | 0.2500 | 0.0400 |
|  |  | 108.200 | 0.030 | 0.2500 | 0.0110 |
|  |  | 111.400 | 0.030 | 0.3200 | 0.0150 |
|  |  | 116.000 | 0.030 | 1.5500 | 0.0150 |
|  |  | 124.400 | 0.030 | 0.2200 | 0.0150 |
|  |  | 138.200 | 0.030 | 0.2000 | 0.0150 |
|  |  | 144.700 | 0.050 | 0.1300 | 0.0070 |
|  |  | 149.900* | 0.020 | 0.7300 | 0.0400 |
|  |  | 153.500 | 0.050 | 0.1500 | 0.0090 |
|  |  | 157.200 | 0.020 | 0.3500 | 0.0220 |
|  |  | 171.300 | 0.020 | 0.1000 | 0.0220 |
|  |  | 187.700 | 0.050 | 0.5500 | 0.0300 |

*Nuclide Library Editor. Genie 2000, Canberra Industries.

3.4.3 Radiochemical Purity by ITLC
3.4.3.1 Described in 3.3.4 above
3.4.4 Radiochemical Purity by Size Exclusion HPLC
3.4.4.1 Take an aliquot from the construct so that the count rates in the peaks are significant above the background of the radioactivity detector
3.4.4.2 Run the sample through the SE-HPLC using the same conditions as in the calibration experiments: 0.9% NaCl, 1 mL/min speed, etc.
3.4.4.3 Compare and calculate the activity associated with the conjugate against the total activity detected by the detector. As illustration, refer to FIG. 6.
3.4.4.4 Calculate the radiochemical purity of the conjugate "Rc" by using the following formula:

$$R_c(\%) = (I_c) * 100\% / I_t$$

Where,
$R_c$=radiochemical purity of the labelled conjugate in %
$I_c$=area measured under the conjugate peak on the SE-HPLC/rad. chromatogram (FIG. 6)
$I_t$=total area measured on the SE-HPLC/rad. chromatogram (FIG. 6)
Calculate the percentage of Ac-225 associated high MW aggregates by using the following formula:

$$A_H(\%) = (I_h) * 100\% / I_t$$

Where,
$A_H$=percentage of Ac-225 associated with high MW aggregates, %
$I_h$=area measured on the left side of the conjugate peak on the SE-HPLC/radioactive chromatogram
Calculate the percentage of Ac-225 associated low MW aggregates by using the following formula:

$$A_L(\%) = (I_l) * 100\% / I_t$$

Figure 3:
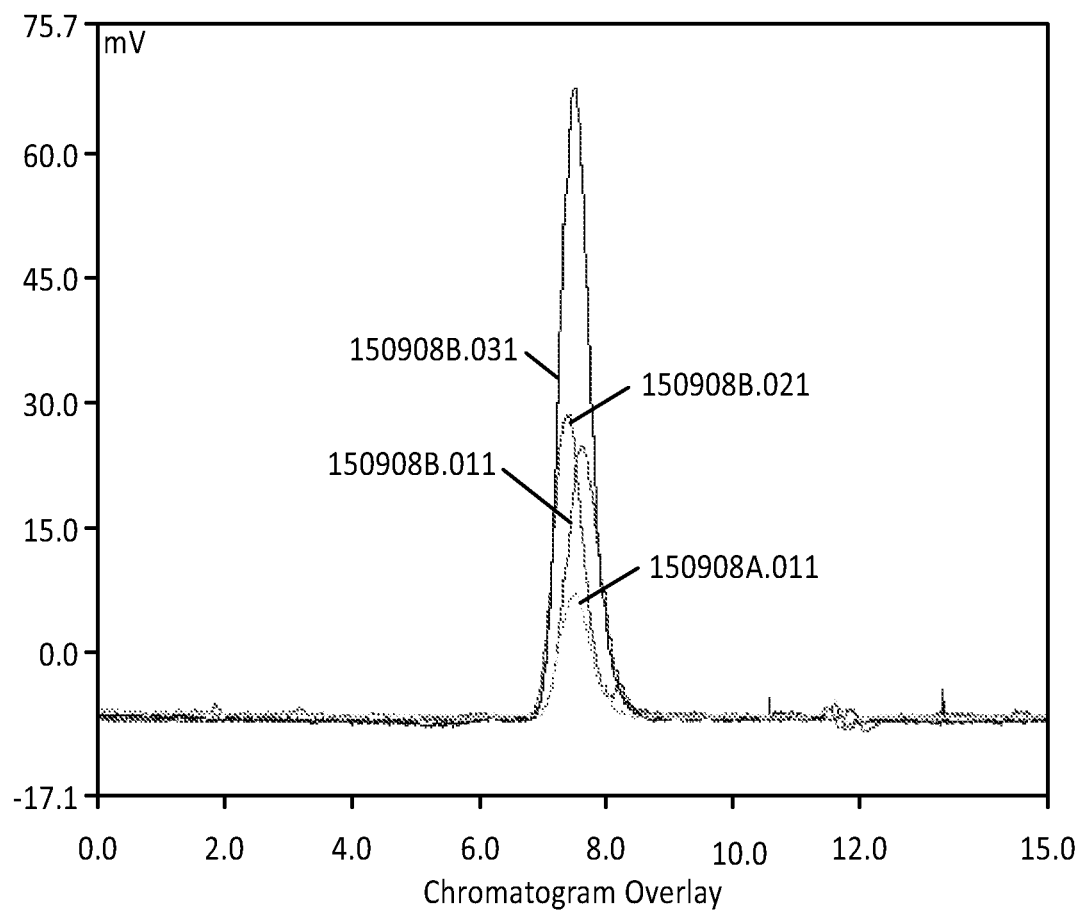
FIG. 3 Calibration of the HPLC with the UV detector for quantification of HuM-195.
Figure 6:
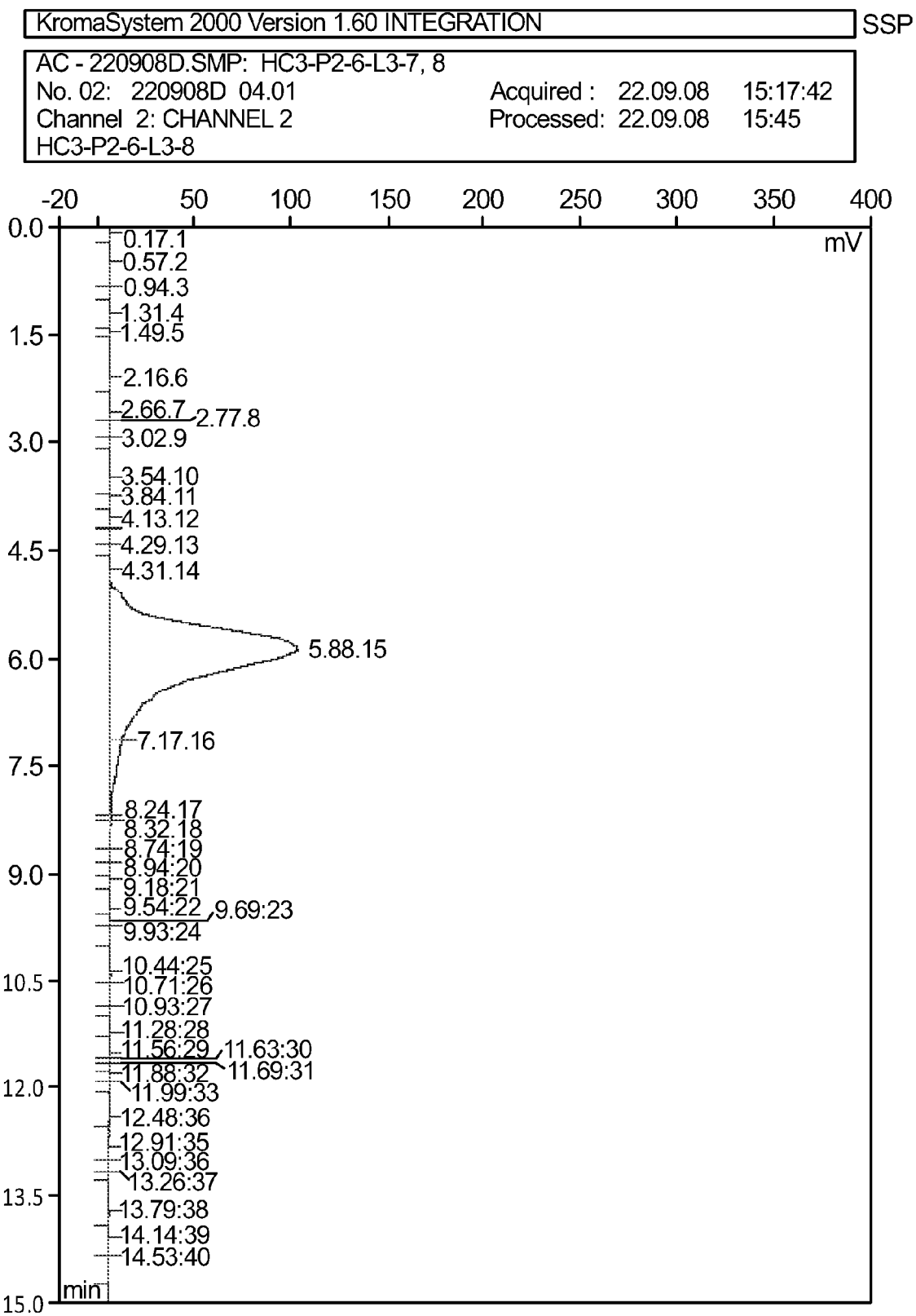
FIG. 6 SE—HPLC/rad. chromatogram of the conjugate (main protein fraction after purification) labelled with Ac-225.
Figure 7:
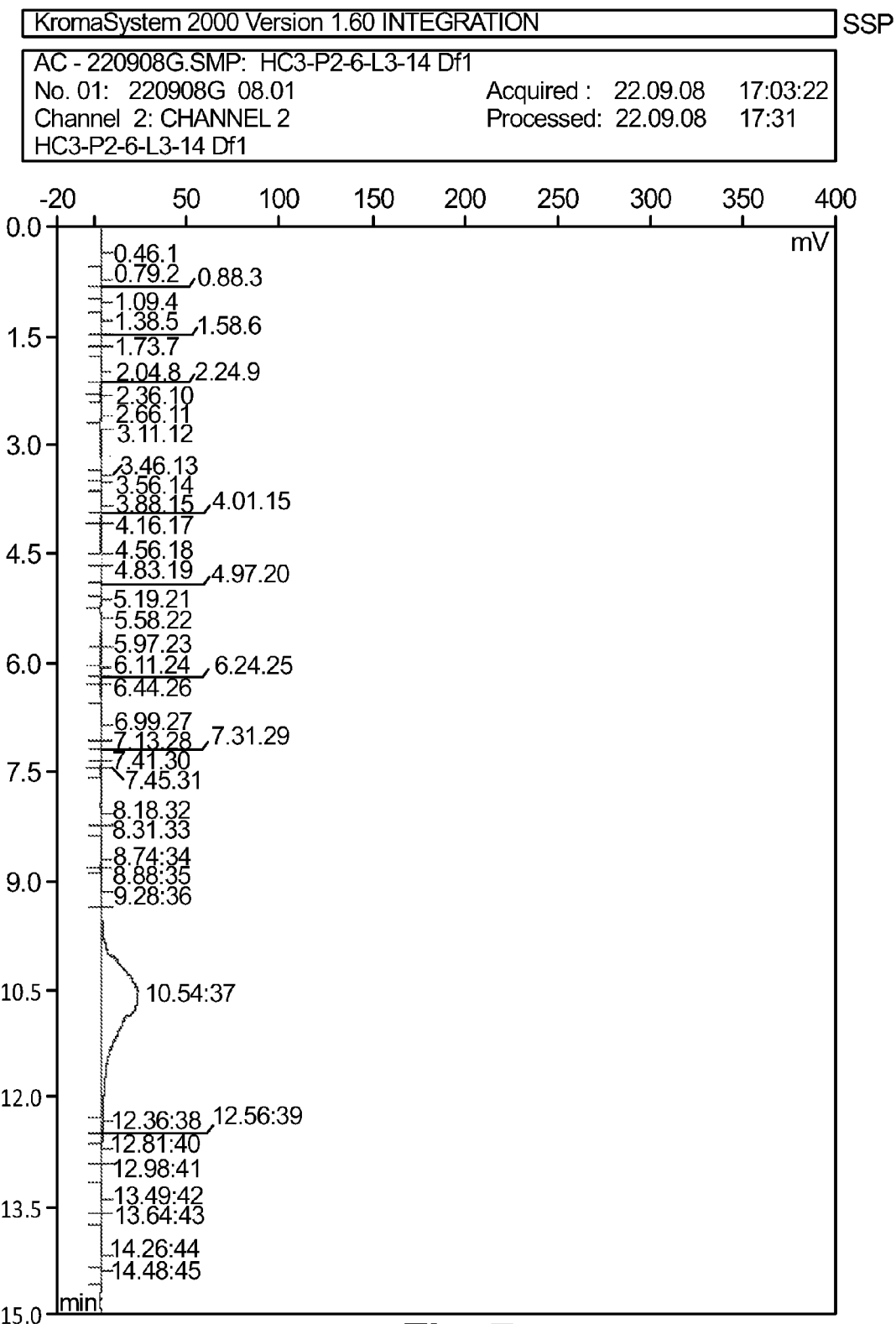
FIG. 7 SE—HPLC/rad. chromatogram of a fraction containing free or DTPA-associated Ac-225.
Figure 8:
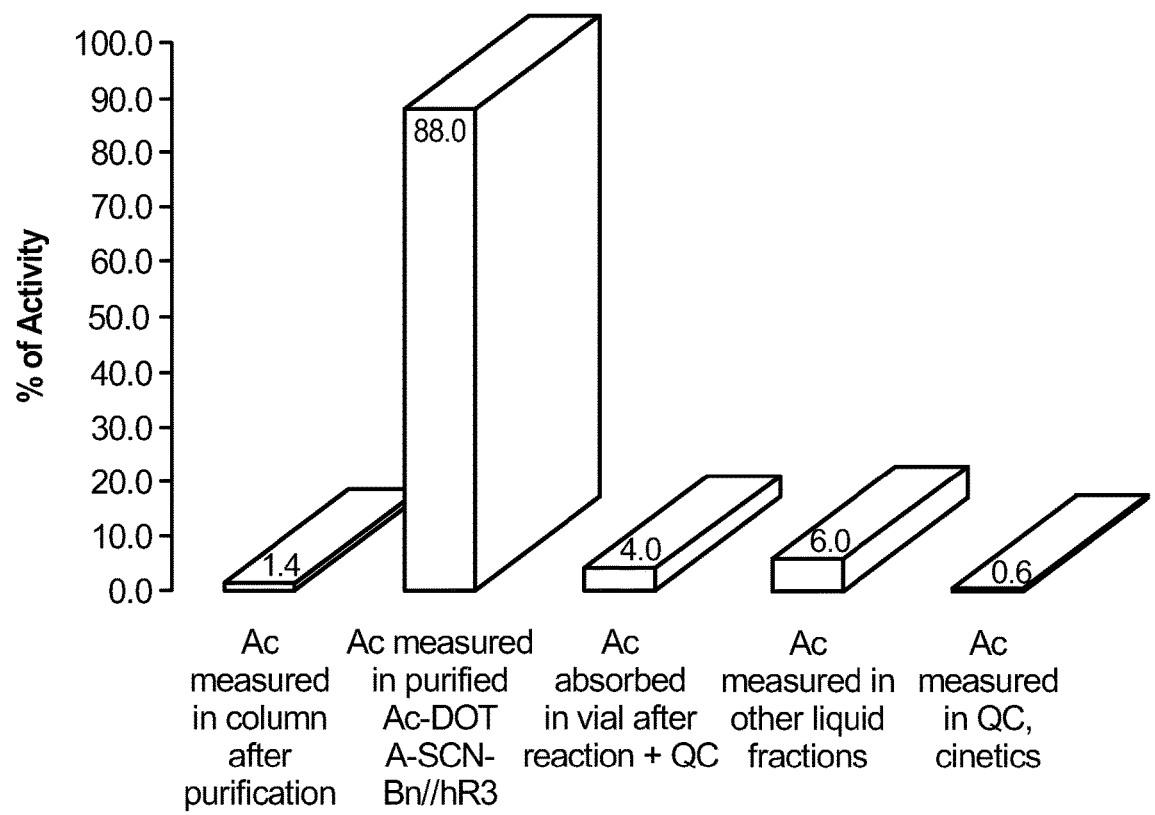
FIG. 8 Typical activity distribution of Ac-225 in liquid fractions after purification, in the P-10 column and in reactor vial+QC (total activity of 1.2 mCi Ac-225).

Where,
$A_L$=percentage of Ac-225 associated with low MW aggregates, %
$I_r$=area measured on the right side of the conjugate peak until the beginning of peak corresponding to free Ac-225, FIG. 6
3.4.5 Immunoreactivity
3.4.5.1 Immunoreactivity of the 225Ac-HuM195 is determined by incubating approximately 2 ng of radiolabeled antibody in 0.030 mL total volume with a 500- to 1000-fold excess of antigen (approximately 10×106 CD33-positive AL67 cells).
These cells express approximately 400,000 CD33-positive binding sites per cell and are in antigen excess to added HuM-195. After 30 minutes incubation at 0° C., the cells are collected by centrifugation and the supernatant removed, the cells are washed once with phosphate buffered saline (PBS) and this wash removed. The cell pellet, supernatant and wash are measured for radioactivity by scintillation counting. The percent immunoreactivity is calculated as equal to {(225Ac-HuM195 bound to cells)/(total bound plus unbound activity (supernatant and wash)} times 100.
3.4.6 Activity of Ac-225 in the Vial
3.4.6.1 Wait more than 6 hours for radioactive equilibrium between 225Ac and all daughters and measure the activity of 225Ac through both 221Fr and 213Bi for final evaluation.
3.4.7 Total Volume of the Construct
3.4.7.1 The total volume of the product is measured gravimetrically
3.4.8 Calculation of the Ac-225 Activity Concentration
3.4.8.1 Calculate the activity concentration (mCi/mL) by dividing the activity obtained in 3.4.6.1 by the volume obtained in 3.4.7.1
3.4.9 Calculation of the Specific Activity
3.4.9.1 Follow as indicated in section 3.3.5.5

3.4.10 Optional: Determination of Protein by UV Spectrophotometry and Calculation of the Specific Activity This method should be used only if HSA is not present in the purified protein fraction (See FIG. 1B).

3.4.10.1 From the combined protein fraction "fp" (section 3.3.6.6) take a 0.02 mL aliquot and bring the volume to 0.5 mL (Df=25) with 0.9% NaCl. A dilution factor Df of 25 is recommended when 1 mg of conjugate is used for labelling.

3.4.10.2 Measure the protein concentration (cpi) in the combined and concentrated sample as described in section 2.3.7 or 2.3.9.

Example 4

TABLE 5

Comparison of manufacturing procedures for the production of Lintuzumab-Ac225 "one step" process vs. existing process

| Test | Specification | "One step" process | Existing process |
| --- | --- | --- | --- |
| Yield | N/A | 84 ± 17.9% | 7.7 ± 2.05% |
| ITLC | ≥95% Lintuzumab-Ac225 | Pass | Pass |
| HPLC | ≥90% HuM195 | Pass | Pass |
| | ≤5% high MW aggregates | Pass | Pass |
| | ≤10% low MW aggregates | Pass | Pass |
| Immunoreactivity | ≥60% active | Pass | Pass |

REFERENCES

Meares C. F., McCall M. J., Rearan D. T., Goodwin D. A., Diamanti C. I., McTigue M. (1984) Conjugation of antibodies with bifunctional chelating agents: isothiocyanate and bromoacetamide reagents, methods of analysis and subsequent addition of metal ions. Anal Biochem; 142: 68-78.

Shrikant V. D., Sally J. D., David L. K., Min K. M., Michael J. Mc., Gerald L. D. y Meares C. F. (1990) Yttrium-90-Labeled monoclonal antibody for therapy: Labeling by new macrocyclic bifunctional chelating agent. J Nucl Med. 31, 473-479.

Michael R. Lewis, Andrew Raubitschek and John E. Shively. (1994) A Facile, Water-Soluble Method for Modification of Proteins with DOTA. Use of Elevated Temperature and Optimized pH To Achieve High Specific Activity and High Chelate Stability in Radiolabeled Immunoconjugates. Bioconjugafe Chem. 5, 565-576.

D. R. Beckford, A. Xiques, R. Leyva, M. Perez-Malo; E. Casanova, M. Barrabi (2007) Nuevo radioimmunoconjugado $^{90}$Y-DOTA-HR3Sintesis y radiomarcaje. Nucleus 2007, 41, 3-8.

Michael R. L., Jim Y. K., Anne-Line J. A., John E. S., and Andrew R. (2001) An improved method for conjugating monoclonal antibodies with N-hydroxysulfosuccinimimidyl DOTA. Bioconjugate Chem. 12, 320-324.

Yasushi Ogawa, Joseph Traina, Eike Zimmermann, Tao Yu, Douglas W. Schneider, Erno Pungor Jr. (2007) Quantification of bifunctional diethyenetriaminepentaccetic acid derivative conjugation to monoclonal antibodies by matrix-assisted laser desorption/ionization time of flight mass spectrometry. Analytical Biochemistry 368 214-221.

Sharon X. Lu, Edward J. Takach, Marjorie Solomon, Qing Zhu, Say-Jong Law, Frank Y. Hsieh (2005) Mass Spectral Analyses of Labile DOTA-HNS and Heterogeneity Determination of DOTA or DM1 Conjugated Anti-PSMA Antibody for Prostate Cancer Therapy. Journal of Pharmaceutical Sciences, Vol. 94, No 4, April 2005.

Instructions 52-1308-00 BB: PD-10 Desalting Column, GE Healthcare. Amicon Centricon Centrifugal Filter Devices. Data sheet Millipore [Ac-225]-DOTA-Hum195 Manufacturing Protocol (Two step labelling procedure), MSKCC Labelling of Hum-195/DOTA conjugates with Ac-225 using the one step method, TUM report, February 2009.

What is claimed is:

1. A method for producing an actinium-225 (Ac-225) radioconjugate, the method comprising the steps of:
    (a) conjugating a chelating agent to a biological molecule in a conjugation reaction mixture having a pH of about 8.0 to about 9.1 to generate a conjugated biological molecule,
    (b) purifying the reaction mixture so as to remove unconjugated chelating agents, and
    (c) chelating one or more Ac-225 radionuclides with the conjugated biological molecule in a chelation reaction mixture having a pH of 5.5-7.0 at 37±2° C., to generate a Ac-225 radioconjugate.

2. The method of claim 1, wherein the conjugating in step (a) comprises incubating the conjugation reaction mixture for about 1.5 hours at about 37° C.

3. The method of claim 1, wherein the conjugating in step (a) comprises incubating the conjugation reaction mixture for about 24 hours at about 16° C. to about 20° C.

4. The method of claim 1, wherein the conjugation reaction mixture comprises a bicarbonate buffer.

5. The method of claim 1, wherein the conjugation reaction mixture comprises a phosphate buffer.

6. The method of claim 1, wherein said purifying comprises filtering in a HEPES buffer.

7. The method of claim 1, wherein said purifying comprises filtering in a NaAc buffer.

8. The method of claim 1, wherein said purifying comprises filtering, wherein said filtering comprises a molecular weight cut off at least about 10,000 Da, at least about 20,000 Da, or at least about 40,000 Da.

9. The method of claim 1, wherein the chelation reaction mixture comprises gentisic acid or ascorbic acid.

10. The method of claim 1, wherein the chelating in step (c) comprises incubating the one or more Ac-225 radionuclides with the conjugated biological molecule for about 1.5 hours at about 37° C.

11. The method of claim 1, further comprising a step of adding a termination chelator to the chelation reaction mixture.

12. The method of claim 11, wherein the termination chelator is diethylenetriamine-pentaacetic acid (DTPA).

13. The method of claim 11, further comprising a step of incubating the chelation reaction mixture for about 30 minutes at about 37° C. following the step of adding the termination chelator.

14. The method of claim 1, wherein the biological molecule comprises a protein, a peptide, a polynucleotide, a combination thereof, or a derivative thereof.

15. The method of claim 1, wherein the biological molecule is an antibody, an antigen-binding fragment thereof, a single-chain protein comprising the antigen-binding polypeptide sequences of an antibody, a single-domain antibody, an analog of any of the foregoing, or a derivative of any of the foregoing.

16. The method of claim 15, wherein the antigen binding fragment is a monoclonal antibody variable region.

17. The method of claim 1, wherein the biological molecule is a protein comprising an antigen binding sequence of an antibody.

18. The method of claim 1, wherein the biological molecule is a naturally, synthetically, or recombinantly produced protein comprising an antigen binding sequence of an antibody that binds an antigen on the surface of a cell.

19. The method of claim 18, wherein the antigen on the surface of the target cell is CD-33.

20. The method of claim 1, wherein the biological molecule is HuM195.

21. The method of claim 1, wherein the radioconjugate is a radioimmunoconjugate.

22. The method of claim 1, wherein the chelating agent is a bifunctional chelating agent.

23. The method of claim 22, wherein the bifunctional chelating agent is S-2-(4-Isothiocyanatobenzyl)-1,4,7,10 tetraazacyclododecanetetraacetic acid (p-SCN-Bn-DOTA).

24. The method of claim 1, wherein the chelating agent is selected from the group of compounds consisting of diethylenetriamine-pentaacetic acid ("DTPA"); 1,4,7,10-tetraazacyclododecane-N,N',N'',N'''-tetraacetic acid ("DOTA"); p-isothiocyanatobenzyl-1,4,7,10-tetraazacyclododecan-1,4,7,10-tetraacetic acid ("pSCN-Bz-DOTA"); 1,4,7,10-tetraazacyclododecane-N,N',N''-triacetic acid ("D03A"); 1,4,7,10-tetraazacyclododecane-1,4,7, 10-tetrakis(2-propionic acid) ("DOTMA"); 3,6,9-triaza-12-oxa-3,6,9-tricarboxymethylene-10-carboxy-13-phenyl-tridec-anoic acid ("B-19036"); 1,4,7-triazacyclononane-N,N',N''-triacetic acid ("NOTA"); 1,4,8,11-tetraazacyclotetradecane-N,N',N'',N'''-tetraacetic acid ("TETA"); triethylene tetraamine hexaacetic acid ("TTHA"); trans-1,2-diaminohexane tetraacetic acid ("CYDTA"); 1,4,7,10-tetraazacyclododecane-1-(2-hydroxypropyl)4,7,10-triacetic acid ("HP-DO3A"); trans-cyclohexane-diamine tetraacetic acid ("CDTA"); trans(1,2)-cyclohexane diethylene triamine pentaacetic acid ("CDTPA"); 1-oxa-4,7,10-triazacyclododecane-N,N',N''-triacetic acid ("OTTA"); 1,4,7,10-tetraazacyclododecane-1,4,7,10-tetrakis{3-(4-carboxyl)-butanoic acid}; 1,4,7,10-tetraazacyclododecane-1,4,7,10-tetrakis(acetic acid-methyl amide); 1,4,7,10-tetraazacyclododecane-1,4,7,10-tetrakis(methylene phosphonic acid); 2,2',2''-(10-(2-(2,5-dioxopyrrolidin-1-yloxy)-2-oxoethyl)-1,4,7,10-tetraazacyclododecane-1,4,7-triyl)triacetic acid (DOTA-NHS ester) and derivatives, analogs, and mixtures thereof.

25. A method for producing an [Ac-225]-p-SCN-Bn-DOTA/HuM195 radioimmunoconjugate, the method comprising the steps of:

(a) conjugating p-SCN-Bn-DOTA to a HuM195 antibody in a conjugation reaction mixture comprising a bicarbonate buffer and having a pH of about 8.0 to about 9.2, for about 1.5 hours at about 37° C. to generate a p-SCN-Bn-DOTA/HuM195 immunoconjugate, (b) filtering the conjugation reaction mixture through a filter having a molecular weight cut off at least about 10,000 Da, at least about 20,000 Da, or at least about 40,000 Da so as to purify the p-SCN-Bn-DOTA/HuM195 immunoconjugate, wherein the filtering is performed with a HEPES buffer or NaAc buffer, (c) chelating one or more actinium-225 radionuclides with the p-SCN-Bn-DOTA/HuM195 immunoconjugate in a chelation reaction mixture comprising gentisic acid and having a pH of about 5.5 to about 7.0, for about 1.5 hours at about 37° C. to generate an [Ac-225]-p-SCN-Bn-DOTA/HuM195 radioimmunoconjugate, (d) adding DTPA to the chelation reaction mixture, and (e) incubating the chelation reaction mixture for about 30 minutes at about 37° C., wherein the yield of the [Ac-225]-p-SCN-Bn-DOTA/HuM195 radioimmunoconjugate is at least 80%.

26. The method of claim 1 or claim 25, further comprising a step of size-exclusion chromatography through a size exclusion resin before step (b).

27. The method of claim 26, wherein the size exclusion resin has a size exclusion limit of about 5000 Da.

28. The method of claim 1, further comprising purifying the radioconjugate by size exclusion chromatography through a size exclusion resin.

29. The method of claim 25, further comprising purifying the [Ac-225]-p-SCN-Bn-DOTA/HuM195 radioimmunoconjugate by size exclusion chromatography through a size exclusion resin.

30. The method of claim 28 or 29, wherein the size exclusion resin has a size exclusion limit of about 6000 Da.

31. The method of claim 28 or 29, wherein the size exclusion resin has a size exclusion limit of about 5000 Da.

32. An Ac-225 radioimmunoconjugate produced by the method of claim 1 or claim 25.

33. The method of claim 1 or 25, wherein the chelation reaction mixture comprises Na acetate or NH4 acetate.

34. The method of claim 33, wherein the concentration of the Na acetate or the NH4 acetate is about 3M.

35. The method of claim 15, wherein the biological molecule is an antibody.

* * * * *